United States Patent [19]

Ueda et al.

[11] 4,367,238

[45] Jan. 4, 1983

[54] PHENYL-ALKANOIC ACID DERIVATIVE AND PREPARATION THEREOF

[75] Inventors: Ikuo Ueda, Toyonaka; Yoshihiko Kitaura, Sakurai; Masaaki Matsuo, Toyonaka; Nobukiyo Konishi, Mukou, all of Japan

[73] Assignee: Fujisawa Pharmaceutical Company, Ltd., Osaka, Japan

[21] Appl. No.: 226,908

[22] Filed: Jan. 21, 1981

[30] Foreign Application Priority Data

Jan. 28, 1980 [GB] United Kingdom ............... 8002790
Dec. 8, 1980 [GB] United Kingdom ............... 8039308

[51] Int. Cl.³ ................ C07D 307/83; A61K 31/365
[52] U.S. Cl. ................................ 424/279; 424/274; 549/269; 549/289; 549/307; 548/463; 548/525
[58] Field of Search .................... 424/279, 274; 260/343.3 R, 343.44, 326 A, 343.41, 326 S, 343.45, 326.36

[56] References Cited

U.S. PATENT DOCUMENTS 2,838,522  6/1958  Wheeler et al. ............. 260/343.3 R
4,120,871  10/1978  Gates et al. ................. 260/343.3 R

FOREIGN PATENT DOCUMENTS 527155  10/1972  Switzerland ...................... 562/478

OTHER PUBLICATIONS

McOmie, Protective Groups in Organic Chemistry, Plenum Press, pp. 66-77.

Primary Examiner—Jane T. Fan
Attorney, Agent, or Firm—Oblon, Fisher, Spivak, McClelland & Maier

[57] ABSTRACT

This invention relates to new phenyl-alkanoic acids, their derivatives at the carboxy group, and pharmaceutically acceptable salts thereof, which have anti-inflammatory, analgesic and antipyretic activities.

8 Claims, No Drawings

PHENYL-ALKANOIC ACID DERIVATIVE AND PREPARATION THEREOF

This invention relates to new phenyl alkanoic acid, its derivative at the carboxy group, and pharmaceutically acceptable salt thereof, which have antiinflammatory, analgesic and antipyretic activities, and an intermediate for preparing the same, to processes for preparation thereof and to pharmaceutical composition comprising the same.

The phenyl-alkanoic acid of this invention can be represented by the formula:

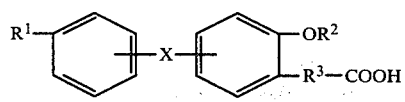 [I]

wherein:
$R^1$ is hydrogen, halogen, hydroxy, lower alkyl or lower alkoxy,
$R^2$ is hydrogen, lower alkyl or acyl,
$R^3$ is alkylene or lower alkenylene optionally substituted with cyano, amino or protected amino group, and
X is O, S, SO or $SO_2$.

It is to be understood that the term "lower" used in connection with the alkyl and alkoxy group in this specification is intended to mean the one having up to seven carbon atoms.

With regard to the groups as defined in the above, the more detailed explanation and preferred examples thereof are given in the following.

The "halogen" for $R^1$ may be fluorine, chlorine, bromine or iodine.

The "lower alkyl" for $R^1$ and $R^2$ may include the straight or branched one such as methyl, ethyl, propyl, isopropyl, butyl, isobutyl, t-butyl, pentyl, hexyl or the like, in which the $C_{1-4}$ alkyl is preferable.

The "lower alkoxy" for $R^1$ may include the straight or branched one such as methoxy, ethoxy, propoxy, isopropoxy, butoxy, isobutoxy, t-butoxy, pentyloxy, hexyloxy or the like, in which the $C_{1-4}$ alkoxy is preferable.

The "acyl" for $R^2$ may be a residue of a carboxylic acid or sulfonic acid and preferably may include lower alkanoyl (e.g. formyl, acetyl, propionyl, butyryl, isopropionyl, isobutyryl, pentanoyl, hexanoyl, etc.), lower alkanesulfonyl (e.g. mesyl, ethanesulfonyl, propanesulfonyl, butanesulfonyl, etc.), aroyl (e.g. benzoyl, toluoyl, xyloyl, naphthoyl, etc.), arenesulfonyl (e.g. tosyl, etc.), and the like, in which lower alkanoyl is preferable and $C_{1-4}$ alkanoyl is more preferable.

The "alkylene" for $R^3$ may include the straight or branched one such as methylene, ethylene, trimethylene, methylmethylene, ethylmethylene, propylmethylene, butylmethylene, pentylmethylene, hexylmethylene, heptylmethylene, octylmethylene, nonylmethylene, decylmethylene, propylene, ethylethylene, propylethylene or the like, in which $C_{1-8}$ alkylene is preferable.

The "lower alkenylene" for $R^3$ may include the straight or branched one such as vinylene, propenylene, butenylene, or the like, in which vinylene is preferable.

These alkylene and lower alkenylene may be substituted with cyano, amino or protected amino group. The protective group in the protected amino group may be a conventional N-protective group such as ar(lower)alkyl (e.g. benzyl, benzhydryl, trityl, etc.), lower alkanoyl (e.g. formyl, acetyl, chloroacetyl, trifluoroacetyl, etc.), lower alkoxycarbonyl (e.g. methoxycarbonyl, ethoxycarbonyl, t-butoxycarbonyl, etc.), ar(lower)alkoxycarbonyl (e.g. benzyloxycarbonyl, benzhydryloxycarbonyl, etc.), succinyl, phthaloyl, or the like.

The derivative at the carboxy group of the compound [I] may include an ester and amide.

The suitable ester may be lower alkyl ester, intramolecular ester, or the like, in which the lower alkyl moiety may be the same as those exemplified above, and the intramolecular ester can be represented by the formula:

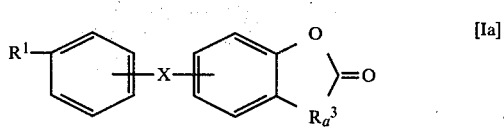 [Ia]

wherein:
$R^1$ and X are each as defined above, and
$R_a^3$ is alkylene optionally substituted with a protected amino group.

The "pharmaceutically acceptable salt" of the object compound [I] may be a conventional one and may include a salt with an inorganic base or acid, for example, a metal salt such as an alkali metal salt (e.g. sodium salt, potassium salt, etc.), an alkaline earth metal salt (e.g. calcium salt, megnesium salt, etc.), ammonium salt, an inorganic acid salt (e.g. hydrochloride, hydrobromide, sulfate, phosphate, carbonate, bicarbonate, etc.), a salt with an organic base or acid, for example, an amine salt (e.g. trimethylamine salt, triethylamine salt, pyridine salt, procaine salt, picoline salt, dicyclohexylamine salt, N,N'-dibenzylethylenediamine salt, N-methylglucamine salt, diethanolamine salt, triethanolamine salt, tris(hydroxyethylamino)methane salt, phenethylbenzylamine salt, etc.), a carboxylic or sulfonic acid salt (e.g. acetate, maleate, lactate, tartrate, mesylate, benzenesulfonate, tosylate, etc.), a basic or acidic amino acid salt (e.g. arginine salt, aspartic acid salt, glutamic acid salt, lysine salt, serine salt, etc.), and the like.

The object compound [I] of this invention can be prepared by the processes as illustrated below:

Process 1

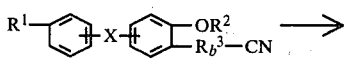 [II]

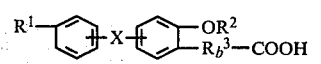 [Ib]

Process 2

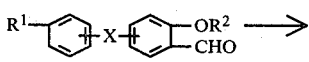 [III]

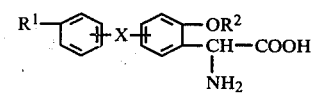 [Ic]

Process 3

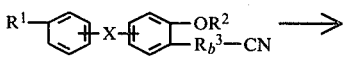 [IV]

-continued

[Id]
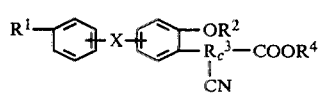

Process 4

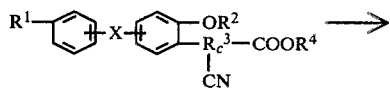

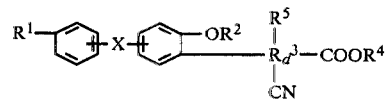

Process 5

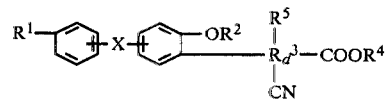

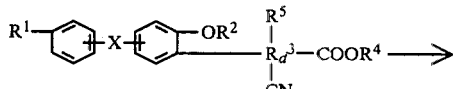

Process 6

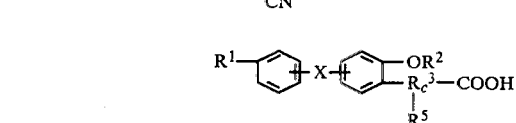

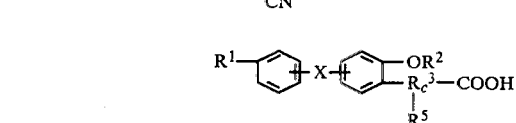

Process 7

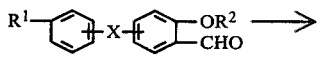

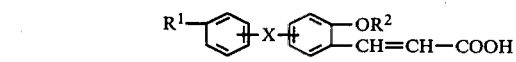

Process 8

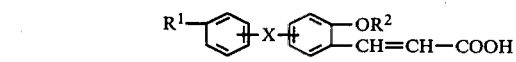

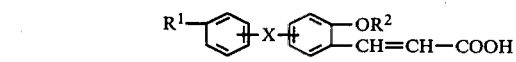

Process 9

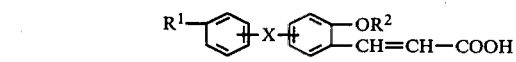

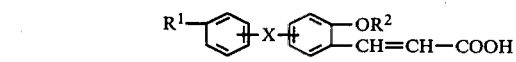

Process 10

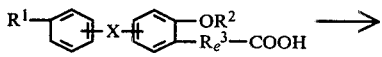

-continued

[Ia]
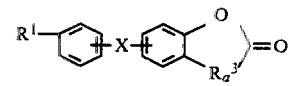

Process 11

[Id]
[V]

[Im]
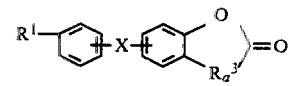

Process 12

[Ia]
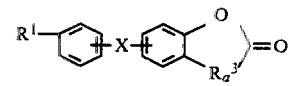

[In]
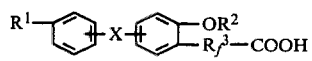

Process 13

[If]
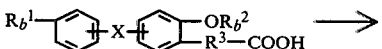
[Io]

[Ip]
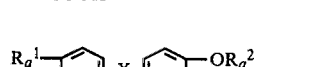

wherein:

$R^1$, $R^2$, $R^3$ and $R_a^3$ are each as defined above, $R_a^1$ and $R_a^2$ are the same as $R^1$ and $R^2$ respectively, provided that at least one of $R_a^1$ and $OR_a^2$ is hydroxy group, $R_b^1$ and $R_b^2$ are the same as $R^1$ and $R^2$ respectively, provided that at least one of $R_b^1$ and $OR_b^2$ is lower alkoxy group, $R_b^3$ is alkylene or lower alkenylene optionally substituted with amino or protected amino group, $R_c^3$ is alkan-triyl or lower alken-triyl, $R_d^3$ is alkan-tetrayl or lower alken-tetrayl, $R_e^3$ is lower alkenylene optionally substituted with cyano, amino or protected amino group, $R_f^3$ is lower alkylene optionally substituted with cyano amino or protected amino group, $R^4$ and $R^5$ is alkyl, X is O, S, SO or $SO_2$, $X_a$ is S, and $X_b$ is SO or $SO_2$.

The processes as shown in the above are explained in detail in the following.

Process 1

A compound [Ib] and its salt can be prepared by hydrolyzing a nitrile compound [II] or its salt.

The salt of the compound [II] may be the same as those of the compound [I].

The hydrolysis can be conducted in a conventional manner, preferably in the presence of a base (e.g. sodium hydroxide, potassium hydroxide, etc.) or acid (e.g. hydrochloric acid, acetic acid, etc.) in a solvent such as water, an organic solvent (e.g. methanol, ethanol, etc.) or an optional mixture thereof, under warming or heating.

In case that a compound [II] where R² is an acyl group is used as a starting material in this process, said acyl group is occasionally removed by this reaction, and such case is also included in this process.

Process 2

A glycine compound [Ic] and its salt can be prepared by treating an aldehyde compound [III] with alkali metal cyanide in the presence of ammonia and then hydrolyzing the resultant nitrile compound.

The alkali metal cyanide used in the first step of this process may be sodium cyanide, potassium cyanide or the like, and this reaction is preferably conducted in a solvent such as water, water-miscible solvent (e.g. methanol, ethanol, dioxane, tetrahydrofuran, etc.) or an optional mixture thereof, at ambient temperature.

The second step of this process can be conducted in a similar manner to the above Process 1.

These first and second steps can be conducted successively without isolating the intermediate compound.

Process 3

A compound [Id] can be prepared by reacting a compound [IV] with di(lower)alkyl carbonate in the presence of a base.

The di(lower)alkyl carbonate to be used in this process may be dimethyl carbonate, diethyl carbonate, dipropyl carbonate or the like, and diethyl carbonate is preferably employed.

The base to be used in this process may be the strong ones such as alkali metal alkoxide (e.g. sodium methoxide, sodium ethoxide, potassium methoxide potassium ethoxide, etc.), or the like, and sodium ethoxide is preferably employed. This reaction is preferably conducted in an organic solvent such as toluene, xylene, or the like, under heating.

Process 4

A compound [Ie] can be prepared by reacting a compound [Id] with an alkylating agent.

The preferable alkylating agent is alkyl halide such as methyl iodide, methyl bromide, ethyl iodide, ethyl bromide, propyl iodide, propyl bromide, butyl iodide, pentyl chloride, hexyl bromide, heptyl bromide, or the like.

This reaction can preferably be conducted in the presence of a strong base such as alkali metal hydride (e.g. sodium hydride, potassium hydride, etc.) or the like, in a solvent such as dimethylformamide, toluene, xylene or the like, at a temperature range from cooling to warming.

Process 5

A compound [If] and its salt can be prepared by hydrolyzing a compound [Ie] and then subjecting the reaction product to decarboxylation reaction.

This process may be preferably conducted by treating a compound [Ie] or its salt with a base (e.g. sodium hydroxide, potassium hydroxide, etc.) or an acid (e.g. hydrochloric acid, acetic acid, etc.) in a solvent such as water, water-miscible solvent (e.g. methanol, ethanol, etc.) or an optional mixture thereof, under heating.

The abovementioned Processes 3,4 and 5 are preferably employed successively for preparing a compound [If] from a compound [IV].

Process 6

A compound [Ig] and its salt can be prepared by reacting an aldehyde compound [III] with malonic acid and then subjecting the resultant product to decarboxylation reaction.

The first step of this process may be preferably conducted in the presence of a strong base such as piperidine, pyrrolidine, 1,5-diazabicyclo[5,4,0]undecene-5, 1,5-diazabicyclo[3,4,0]nonene-5, in a solvent such as pyridine, toluene, benzene, tetrahydrofuran, dimethylsulfoxide, dimethylformamide, at ambient temperature. And the second step of this process can be conducted by heating the reaction mixture obtained above.

Process 7

A compound [Ii] and its salt can be prepared by reducing a compound [Ih] or its salt.

The reduction reaction of this process can be preferably conducted by catalytic reduction using a conventional catalyst such as palladium catalyst (e.g. palladium on carbon, etc.), platinum catalyst (e.g. platinum oxide, etc.), rhodium catalyst (e.g. tris-(triphenylphosphine)rhodium chloride, etc.), at ambient temperature under ordinal pressure. This catalytic reduction is usually conducted in a solvent such as dioxane, ethyl acetate, acetic acid, methanol, ethanol or the like.

Process 8

A compound [Ik] and its salt can be prepared by reacting a compound [Ij], its derivative at the carboxy group or a salt thereof with an alkylating agent.

The alkylating agent to be used in this process may be a conventional one such as alkyl halide (e.g. methyl iodide, ethyl bromide, propyl bromide, etc.), diazoalkane (e.g. diazomethane, diazoethane, etc.), dialkyl sulfate (e.g. dimethyl sulfate, diethyl sulfate, etc.) or the like.

This reaction may preferably be conducted in a solvent such as acetone, dioxane, diethyl ether or the like at ambient temperature or under warming or heating.

In case that alkyl halide or dialkyl sulfate is used as an alkylating agent, the reaction is preferably conducted in the presence of a base such as alkali metal carbonate (e.g. sodium carbonate, potassium carbonate, etc.), alkali metal bicarbonate (e.g. sodium bicarbonate, potassium bicarbonate, etc.) or the like.

It is to be noted that the starting compound [Ij] may be an intramolecular ester wherein $R_a^1$ is a hydroxy group.

In case that free carboxylic acid [Ij] is used as a starting material in this process, alkyl ester of the compound [Ik] can occasionally be produced, and said ester compound can be hydrolyzed by conventional method to give a free carboxylic acid [Ik], if desired.

Process 9

A compound [Ij] and its salt can be prepared by treating a compound [Ik] or its salt with an acid.

The suitable acid to be used in this process may be hydrohalogenic acid (e.g. hydriodic acid, hydrobromic acid, etc.), Lewis acid or the like.

This reaction is usually conducted in a solvent such as acetic anhydride, acetic acid, benzene, toluene, carbon disulfide or the like, preferably under anhydrous conditions and heating.

In case that $R_b^1$ and $OR_b^2$ of the starting compound [Ik] are lower alkoxy groups, both of those alkoxy groups are occasionally converted to hydroxy groups, and such case is also included in the scope of this process.

Process 10

A compound [Ia] can be prepared by treating a compound [II] with an acid or its reactive equivalent.

The acid to be used in this process may be inorganic or organic one such as hydrochloric acid, acetic acid, p-toluene sulfonic acid or the like, and the reactive equivalent thereof may be acid anhydride such as acetic anhydride, phthalic anhydride, or the like.

The reaction is usually conducted in a solvent such as benzene, toluene, xylene or the like under warming or heating, and preferably under anhydrous conditions.

In case that the liquid reagent is used in this reaction, said reagent can also be used as a solvent.

When a compound [II] where $R^3$ is alkylene substituted with an amino group is used as a starting material and an acid anhydride is used as a reagent, a compound where $R_a^3$ is alkylene substituted with a protected amino group (i.e. acylimino group) can be produced.

In case that a compound [II] where $R^2$ is lower alkyl group is used as a starting material, this process is conducted by subjecting said compound [II] to the reaction of Process 9 and then treating the reaction product with an acid or its reactive equivalent as exemplified above, and such case is also included in this process. When the acid or its reactive equivalent as exemplified above is used in the first step of this case, the object compound [Ia] can occasionally be produced in one step.

And further, in case that the hydrolysis of the compound [II] is conducted by using an acid as exemplified above, the object compound [Ia] can occasionally be produced in one step, and such case is also included in the scope of this process.

Process 11

A compound [Im] can also be prepared by oxidizing a compound [V] and then treating the reaction product with an acid or its reaction equivalent.

The oxidizing agent to be used in the first step of this process may be a combination of ozone and hydrogen peroxide, or a salt of a per acid such as alkali metal metaperiodate (e.g. potassium metaperiodate, etc.), alkali metal permanganate (e.g. potassium permanganate, etc.), or the like.

This reaction may preferably be conducted in a solvent such as aceitc acid, methanol, ethanol, water, an optional mixture thereof, or the like, at ambient temperature.

And the second step of this process can be conducted substantially in the same manner as the above Process 10.

In case that a compound [V] where $R^2$ is an acyl group is used as a starting material in this process, said acyl group is removed by hydrolysis prior to the above-mentioned second step. The hydrolysis is preferably conducted by using a base such as alkali metal hydroxide (e.g. sodium hydroxide, potassium hydroxide, etc.) or the like in a solvent such as methanol, ethanol or the like, at ambient temperature.

The reactions mentioned above can be conducted successively without isolating the intermediate product.

Process 12

A compound [In] and its salt can be prepared by hydrolyzing a compound [Ia].

The hydrolysis can be conducted in a similar manner to that of Process 1, preferably by using alkali metal hydroxide (e.g. sodium hydroxide, potassium hydroxide, etc.) in alcohol (e.g. methanol, ethanol, etc.) at ambient temperature or under warming or heating.

Process 13

A compound [Ip], its derivative at the carboxy group and a salt thereof can be prepared by reacting a compound [Io], its derivative at the carboxy group or a salt thereof with an oxidizing agent.

The oxidizing agent includes a conventional one which can oxidize a thio group into sulfinyl or sulfonyl group, and preferably may be m-chloroperbenzoic acid, perbenzoic acid, hydrogen peroxide or the like.

This reaction is usually conducted in a conventional solvent such as chloroform, methylenechloride or the like.

All the compounds produced by the above processes can be isolated from the reaction mixture and purified by a conventional method. And, in case that the object product having a free amino and/or carboxy group is obtained as the reaction product in these processes, it may also be transformed into an optional salt thereof as illustrated above by a conventional salt formation method.

The starting compounds to be used in the methods of this invention include novel ones, and can be prepared by the methods as described in the Examples or the methods chemically equivalent thereto.

It can be understood through the following pharmacological test data that the object compound (I) of the present invention exhibits antiinflammatory, analgesic and antipyretic activities and is useful as an antiinflammatory, analgesic and antipyretic agent for human beings and animals.

Test Method (1)

Three, five or ten male 5 week old Hartley rats, each weighing about 350 g. were used per group. The backs of each animal were depilated 24 hours before the test. An adhesive tape with 3 small holes of 9 mm diameter was placed on the depilated skin and then the animal was exposed to ultra-violet radiation from an ultra-violet lamp (500 W, manufactured by Engelhard Hanovia Inc.) at a distance of 13 cm. for 80 seconds. Two hours later, the degree of erythema was estimated on the basis of the following scores:

1.0:erythema with clear border,
0.5:erythema with unclear border,
0.0:scarcely erythema.

The drugs were regarded as being effective when the total of 3 points was below 1.5.

Each dosage of the test compound (1 mg/kg) was administered orally in a suspension form in 20 ml. of 0.5% methyl cellosolve aqueous solution. Half of the test sample was administered one hour before the radiation and the remaining half of the test solution was administered just after radiation. The test results obtained are given in the following Table 1:

TABLE 1

| Test compound obtained in Example | Number of rats estimated as effective/Number of rats used as a group |
|---|---|
| 3-(9) | 8/10 |
| 5-(4) | 10/10 |
| 10-(7) | 3/3 |
| 11-(4) | 3/5 |

Test Method (2): (Rat paw edemas method)

Ten Sprague-Dawley rats were used per group. The right hind paw of the rat was injected subcutaneously under the plantar surface with 0.1 ml of carrageenin (1%), and four and two hours later, respectively, the animals were sacrificed. The normal and edematous hind paws were cut off at the tibiodorsal joint and weighed. The difference in the weight of edematous paw and that of normal paw was a measure of the edema.

The drug was administered orally 60 minutes before the irritating agent. Paw swelling of treated animals was compared with that of control animals.

Test compounds were added at the dose level of 100 mg/kg.

The test results obtained are given in the following Table 2:

TABLE 2

| Test compound obtained in Example | Decrease of paw swelling of treated animals compared with that of control animals (%) |
| --- | --- |
| 3-(9) | 22.6 |
| 5-(4) | 23.1 |
| 5-(6) | 27.5 |
| 10-(7) | 65.5* |
| 11-(4) | 31.1* |
| 13-(3) | 37.4* |
| 14-(8) | 50.4* |
| 21-(9) | 42.6 |
| 22-(4) | 55.4 |
| 29-(11) | 58.0 |

(*: Test animals were fasted for 24 hrs. before administration. Dose level was 10 mg/kg.)

As can be seen from the above test results, the object compounds (I) of the present invention are useful for the antiinflammatory, analgesic and antipyretic medicines such as headache, toothache or pyrexia.

The effective ingredients may usually be administered with a dose of 10 to 500 mg., 1 to 4 times a day in a preparations such as tablet, granule, powder, capsule, syrup, injection, suppository and the like. However, the above dosage may be increased or decreased according to the age, weight or conditions of the patient or the administering method. The abovementioned preparations can be prepared in a conventional manner by using conventional carriers and additives.

The following examples are given for illustrating the present invention in more detail.

EXAMPLE 1

(1) Powdered potassium hydroxide (10.0 g) was added to a solution of guaiacol (24.8 g) in toluene (200 ml) with stirring at room temperature. After stirring the mixture for 30 minutes, toluene was evaporated under ordinal pressure. The residue was dried at 150° C. under reduced pressure. To this product were added 2-methoxy-3-methylbromobenzene (34.40 g) and powdered copper (0.3 g), and the mixture was stirred at 180°–220° C. for 2 hrs. After cooling, the reaction mixture was extracted with diethyl ether. The extract was washed with water, dried over magnesium sulfate and then evaporated. The oily residue was subjected to distillation under reduced pressure to give pale yellow oil of 2-methoxyphenyl 2-methoxy-3-methylphenyl ether (9.20 g). bp 138° C./0.8 mmHg.

I.R. (Film): 1600, 1280, 1260, 1220 cm$^{-1}$.

N.M.R. (CDCl$_3$): δ2.30 (3H, s), 3.80 (3H, s), 3.90 (3H, s), 6.43–7.20 (7H, m).

(2) N-Bromosuccinimide (6.56 g) and 2,2'-azobisisobutyronitrile (100 mg) were added to a solution of 2-methoxyphenyl 2-methoxy-3-methylphenyl ether (9.0 g) in benzene (100 ml), and the mixture was refluxed under heating for 2 hrs. The reaction mixture was evaporated, and water was added to the residue. The mixture was extracted with diethyl ether, and the extract was washed with water, dried over magnesium sulfate and then evaporated to give oily residue of 2-methoxyphenyl 2-methoxy-3-bromomethylphenyl ether (12.10 g).

I.R. (Film): 1600, 1500, 1280, 1260, 1230 cm$^{-1}$.

N.M.R. (CCl$_4$): δ3.73 (3H, s), 4.03 (3H, s), 4.50 (2H, s), 6.50–7.30 (7H, m).

(3) Powdered Potassium cyanide (2.50 g) was added to a solution of 2-methoxyphenyl 2-methoxy-3-bromomethylphenyl ether (12.0 g) in dimethylsulfoxide (100 ml), and the mixture was stirred at room temperature for 1 hr. The reaction mixture was poured into water and extracted with diethyl ether. The extract was washed with water, dried over magnesium sulfate and then evaporated. The resultant oily residue (9.80 g) was subjected to column chromatography on silica gel and eluted with a mixture of benzene and hexane (1:1). The eluate was evaporated to give oily 2-[2-methoxy-3-(2-methoxyphenoxy)phenyl]acetonitrile (6.20 g).

I.R. (Film): 2250 cm$^{-1}$.

N.M.R. (CDCl$_3$): δ3.73 (2H, s), 3.86 (3H, s), 4.06 (3H, s), 6.67–7.40 (7H, m)

(4) A mixture of 2-[2-methoxy-3-(2-methoxyphenoxy)phenyl]acetonitrile (19.6 g), acetic acid (300 ml) and conc. hydrochloric acid (110 ml) was refluxed under heating for 5 hrs.

The reaction mixture was evaporated to dryness, and water was added to the residue. The mixture was extracted with diethyl ether. The diethyl ether solution was extracted with saturated aqueous sodium bicarbonate. The extract was acidified with conc. hydrochloric acid, and precipitating crystals were collected by filtration, washed with water and then dried to give crude crystals (15.7 g). This substance was subjected to column chromatography on silica gel (270 g) and eluted with a mixture of ethyl acetate and chloroform (1:3). The resultant crystals were recrystallized from ethanol to give 2-[2-methoxy-3-(2-methoxyphenoxy)phenyl]acetic acid (11.7 g). mp 121°–122° C.

I.R. (Nujol): 3100, 3040, 2680, 1715, 1615, 1585, 1510, 1490, 1470, 1440, 1420, 1340, 1320, 1300, 1280, 1260 cm$^{-1}$.

N.M.R. (DMSO-d$_6$): δ3.61 (2H, s), 3.80 (3H, s), 3.83 (3H, s), 6.40–7.40 (7H, m).

Analysis for C$_{16}$H$_{16}$O$_5$: Calculated: C: 66.66, H: 5.59; Found: C: 67.18, H: 5.45.

(5) 2-[2-Methoxy-3-(2-methoxyphenoxy)phenyl]acetic acid (10.50 g) was dissolved in a mixture of 48% hydriodic acid (61.5 ml) and acetic anhydride (31.5 ml) and then refluxed under heating for 40 minutes. After cooling, the reaction mixture was evaporated, and the residue was extracted with diethyl ether. The extract was washed with an aqueous sodium hydrogen sulfite and subsequently with saline, dried over magnesium sulfate and then evaporated. The oily residue (11.50 g) was allowed to stand, and the precipitating crystals (11.50 g) were recrystallized from benzene to give colorless crystals of 2-[2-hydroxy-3-(2-hydroxyphenoxy)-phenyl]acetic acid (9.4 g). mp 91°–93° C.

I.R. (Nujol): 3450, 3300, 1690 cm$^{-1}$.

N.M.R. (DMSO-d$_6$): δ3.50 (2H, s), 6.40–7.0 (7H, m).

(6) A mixture of 2-[2-hydroxy-3-(2-hydroxyphenoxy)phenyl]acetic acid (9.4 g) and p-toluene sulfonic acid (0.2 g) in benzene (100 ml) was refluxed under heating for 3 hrs. Benzene (20 ml) was distilled off from the reaction mixture, and benzene (20 ml) was newly added and refluxed again under heating for 3 hrs. The reaction mixture was washed with water, aqueous sodium bicarbonate and saline successively, dried over magnesium sulfate and then evaporated. The precipitates were recrystallized from ethanol (10 ml) to give 7-(2-hydroxyphenoxy)-2,3-dihydrobenzofuran-2-one (6.2 g). mp 150°–152.5° C.

I.R. (Nujol): 3380, 1780, 1635, 1595, 1510, 1490, 1470, 1360, 1295 cm$^{-1}$.

N.M.R. (CDCl$_3$): δ3.80 (2H, s), 5.70 (1H, s), 6.76–7.46 (7H, m).

Analysis for C$_{14}$H$_{10}$O$_4$: Calculated: C: 69.42, H: 4.16; Found: C: 69.56, H: 3.89.

(7) An excess of a solution of diazomethane in diethyl ether was added to a solution of 7-(2-hydroxyphenoxy)2,3-dihydrobenzofuran-2-one (4.9 g) in a mixture of diethyl ether (50 ml) and dioxane (50 ml), and allowed to stand overnight at room temperature. To the reaction mixture was added acetic acid (1 ml), and the organic solvent was distilled off. The oily residue was purified by column chromatography, and the crude crystals were crystallized from ethyl acetate to give 7-(2-methoxyphenoxy)-2,3-dihydrobenzofuran-2-one (2.3 g). mp 171°–172° C.

I.R. (Nujol): 1805, 1640, 1610, 1500, 1475, 1390, 1340, 1310, 1300, 1280, 1265 cm$^{-1}$.

N.M.R. (DMSO-d$_6$): δ3.78 (3H, s), 3.98 (2H, s), 6.54–7.30 (7H, m).

Analysis for C$_{15}$H$_{12}$O$_4$: Calculated: C: 70.30, H: 4.72; Found: C: 70.18, H: 4.38.

(8) A solution of potassium hydroxide (1.3 g) in methanol (30 ml) was added to a solution of 7-(2-methoxyphenoxy)-2,3-dihydrobenzofuran-2-one (1.3 g) in methanol (30 ml), and allowed to stand at room temperature for 3 hrs. Methanol was distilled off from the reaction mixture, and the residue was dissolved in water. The aqueous solution was acidified with conc. hydrochloric acid, and the precipitating crystals were collected by filtration, washed with water, dried and then recrystallized from a mixture of ethyl acetate and n-hexane to give 2-[2-hydroxy-3-(2-methoxyphenoxy)phenyl]acetic acid (1.0 g). mp 125°–126° C.

I.R. (Nujol): 3460, 1690, 1590, 1500, 1480, 1270, 1260 cm$^{-1}$.

N.M.R. (DMSO-d$_6$): δ3.30 (1H, broad s), 3.57 (2H, s), 3.76 (3H, s), 6.33–7.30 (7H, m).

Analysis for C$_{15}$H$_{14}$O$_5$: Calculated: C: 65.69, H: 5.15; Found: C: 65.66, H: 4.99.

EXAMPLE 2

(1) o-Tolyl 2-allyloxyphenyl ether (70 g) was heated at 250° C. with stirring for 30 minutes. To the resultant substance were added pyridine (200 ml) and acetic anhydride (50 g), and the mixture was allowed to stand at room temperature for an hour. The reaction mixture was poured into water (1 l) and extracted with diethyl ether. The extract was washed with dil. hydrochloric acid and water successively, dried over magnesium sulfate and then evaporated. The oily residue (85.0 g) was subjected to distillation under reduced pressure to give colorless oil of o-tolyl 2-acetoxy-3-allylphenyl ether (60.0 g). bp 147°–150° C./0.6 mmHg.

I.R. 1765, 1640, 1280, 1180 cm$^{-1}$.

(2) Ozone gas was introduced into a solution of o-tolyl 2-acetoxy-3-allylphenyl ether (5.64 g) in acetic acid (80 ml) at 15° C. with stirring for 45 minutes. 30% Hydrogen peroxide (4 ml) was added to the solution and allowed to stand overnight at room temperature. Aqueous sodium hydrogen sulfite was added to the solution, and the mixture was extracted with diethyl ether. The extract was washed with water, dried over magnesium sulfate and then evaporated. The oily residue (4.0 g) was dissolved in a mixture of sodium hydroxide and methanol. The solution was allowed to stand at room temperature for 30 minutes, and methanol was distilled off. The residue was washed with diethyl ether, acidified with dil. hydrochloric acid and then extracted with diethyl ether. The extract was dried over magnesium sulfate and evaporated. The oily residue (2.10 g) was dissolved in acetic anhydride (20 ml), heated on a water bath for 10 minutes and then evaporated. The crystalline residue was recrystallized from methanol to give colorless needles of 7-(o-tolyloxy)-2,3-dihydrobenzofuran-2-one (1.10 g). mp 110°–111° C.

I.R. (Nujol): 1790 cm$^{-1}$.

N.M.R. (DMSO-d$_6$): δ2.25 (3H, s), 3.73 (2H, s), 6.63–7.33 (7H, m).

Analysis for C$_{15}$H$_{12}$O$_3$ Calculated: C: 74.98, H: 5.03; Found: C: 75.04, H: 5.01.

EXAMPLE 3

(1) o-Tolyl 2-allyloxyphenyl ether (41.1 g) was heated at 250° C. with stirring for 30 minutes. The resultant oil was subjected to distillation under reduced pressure to give oily 2-allyl-6-(o-tolyloxy)phenol (29.7 g). bp 127°–140° C./1.5 mmHg.

I.R. (Film): 3525, 1640, 1610, 1580, 1490, 1470, 1350, 1265 cm$^{-1}$.

N.M.R. (CDCl$_3$): δ2.27 (3H, s), 3.50 (2H, m), 5.10 (2H, m), 5.70–7.40 (9H, m).

(2) A solution of 2-allyl-6-(o-tolyloxy)phenol (3.0 g) in methanol (10 ml) saturated with potassium hydroxide was refluxed under heating. Methanol was distilled off from the reaction mixture until the inner temperature came to 110° C. Thereafter, the mixture refluxed with stirring at 110° C. for an hour. Water was added to the reaction mixture, acidified with conc. hydrochloric acid and then extracted with diethyl ether. To extract was washed with saline, dried over magnesium sulfate and evaporated. The oily residue (3.1 g) was pulverized and recrystallized from n-hexane to give 2-(1-propenyl)-6-(o-tolyloxy)phenyl (0.55 g). mp 63°–66° C.

I.R. (Nujol): 3520, 1610, 1580, 1500, 1470, 1390, 1360, 1270 cm$^{-1}$.

N.M.R. (CDCl$_3$): δ1.93 (3H, d, J=5 Hz), 2.23 (3H, s), 5.86 (1H, s), 6.53–7.47 (9H, m).

(3) Ozone gas was introduced into a solution of 2-(1-propenyl)-6-(o-tolyloxy)phenol (13.7 g) in a mixture of ethyl acetate (300 ml) and acetic acid (50 ml) at 0°–3° C. with stirring for an hour. The reaction mixture was washed with water, aqueous sodium bicarbonate and saline successively, dried over magnesium sulfate and when evaporated. The oily residue (12.9 g) was dissolved in diethyl ether, and the solution was washed with water, dried over magnesium sulfate and evaporated. The oily residue (11.7 g) was pulverized and recrystallized from methanol to give 2-hydroxy-3-(o-tolyloxy)benzaldehyde (4.8 g). mp 56°–58° C.

I.R. (Nujol): 1650, 1490, 1450, 1390, 1300, 1270, 1250 cm$^{-1}$.

N.M.R. (CDCl$_3$): δ2.33 (3H, s), 6.73–7.60 (7H, m), 10.00 (1H, s), 11.23 (1H, s).

Analysis for C$_{14}$H$_{12}$O$_3$: Calculated: C: 73.67, H: 5.30; Found: C: 73.93, H: 5.15.

(4) 2-Hydroxy-3-(o-tolyloxy)benzaldehyde (64.20 g), dimethyl sulfate (46.10 g) and powdered potassium carbonate (50.50 g) were added to dimethylformamide (150 ml) and stirred at room temperature for 2 hrs. The reaction mixture was poured into water (1 l), and the precipitating crystals were collected by filtration. The aqueous filtrate was extracted with diethyl ether, and the crystals obtained above were dissolved in the extract. The ether solution was washed with water, dried over magnesium sulfate and evaporated. The crystalline residue was recrystallized from methanol to give colorless crystals of 2-methoxy-3-(o-tolyloxy)benzaldehyde (48.70 g). mp 53°–55° C.

I.R. (Nujol): 1680 cm$^{-1}$

N.M.R. (CDCl$_3$): δ2.30 (3H, s), 4.06 (3H, s), 6.66–7.70 (7H, m), 10.40 (1H, s).

(5) Powdered sodium borohydride (7.0 g) was added portionwise to a solution of 2-methoxy-3-(o-tolyloxy)-benzaldehyde (47.50 g) in methanol (100 ml) under cooling with stirring, and the mixture was stirred at the same temperature for 30 minutes.

The reaction mixture was poured into water (1 l), acidified with conc. hydrochloric acid and then extracted with diethyl ether. The extract was washed with water, dried over magnesium sulfate and evaporated to give 2-methoxy-3-(o-tolyloxy)benzyl alcohol (44.0 g). mp 63°–65° C.

I.R. (Nujol): 3350 cm$^{-1}$.

N.M.R. (CDCl$_3$): δ2.27 (3H, s), 3.90 (3H, s), 4.70 (2H, s), 6.56–7.30 (7H, m).

(6) Thionyl chloride (30 ml) and pyridine (1 drop) were added to a solution of 2-methoxy-3-(o-tolyloxy)-benzyl alcohol (44.0 g) in benzene (150 ml). The mixture was refluxed under heating for 40 minutes and then evaporated. The residue was dissolved in diethyl ether, washed with aqueous sodium bicarbonate and water successively, dried over magnesium sulfate and then evaporated to give oily o-tolyl 2-methoxy-3-chloromethylphenyl ether (47.50 g).

I.R. (Film): 1580, 1480, 1280, 1230 cm$^{-1}$.

N.M.R. (CDCl$_3$): δ2.33 (3H, s), 4.03 (3H, s), 4.72 (2H, s), 6.70–7.43 (7H, m).

(7) Powdered potassium cyanide (12.50 g) and sodium iodide (28.80 g) were added to a solution of o-tolyl 2-methoxy-3-chloromethylphenyl ether (47.50 g) in dimethylsulfoxide (100 ml) and stirred at room temperature for 30 minutes. The reaction mixture was poured into water and extracted with diethyl ether. The extract was washed with water 3 times, dried over magnesium sulfate and then evaporated to give only 2-[2-methoxy-3-(o-tolyloxy)phenyl]acetonitrile (44.0 g).

I.R. (Film): 2260 cm$^{-1}$.

N.M.R. (CDCl$_3$): δ2.33 (3H, s), 3.80 (2H, s), 4.06 (3H, s), 6.76–7.51 (7H, m).

(8) 2-[2-Methoxy-3-(o-tolyloxy)phenyl]acetonitrile (43.0 g) was added to a mixture of acetic acid (200 ml) and conc. hydrochloric acid (50 ml), and the mixture ws refluxed under heating for 5 hrs. The reaction mixture was evaporated, and water was added to the residue and extracted with diethyl ether. The extract was washed with water and extracted with aqueous sodium bicarbonate. The aqueous extract was washed with diethyl ether, acidified with conc. hydrochloric acid and then extracted with diethyl ether. The ether extract was dried over magnesium sulfate and evaporated. The crystalline residue (37.50 g) was recrystallized from a mixture of diisopropyl ether and n-hexane to give 2-[2-methoxy-3-(o-tolyloxy)phenyl]acetic acid (34.5 g). mp 90°–92° C.

I.R. (Nujol): 1700 cm$^{-1}$.

N.M.R. (CDCl$_3$): δ2.30 (3H, s), 3.73 (2H, s), 3.90 (3H, s), 6.60–7.33 (7H, m), 10.60 (1H, s).

(9) 2-[2-Methoxy-3-(o-tolyloxy)phenyl]acetic acid (34.0 g) was added to a mixture of acetic anhydride (50 ml) and 50% aqueous solution of hydrogen iodide (100 ml), and the mixture was refluxed under heating for an hour. The reaction mixture was poured into ice-water (1 l) and extracted with diethyl ether. The extract was washed with aqueous sodium hydrogen sulfite and water (twice) successively, dried over magnesium sulfate and then evaporated. The oily residue (34.0 g) was dissolved in acetic anhydride (50 ml), stirred at 100° C. for 1.5 hours and then evaporated. The crystalline residue (29.0 g) was recrystallized from methanol and diisopropyl ether successively to give colorless crystals of 7-(o-tolyloxy)-2,3-dihydrobenzofuran-2-one (22.0 g). mp 110°–111° C.

IR (Nujol): 1790 cm$^{-1}$.

(10) 7-(o-Tolyloxy)-2,3-dihydrobenzofuran-2-one (2.20 g) was dissolved in a solution of potassium hydroxide (2.0 g) in methanol (30 ml), and the solution was allowed to stand at room temperature for an hour. The reaction mixture was evaporated, and the residue was dissolved in water, washed with diethyl ether, acidified with conc. hydrochloric acid and then extracted with diethyl ether. The extract was washed with water, dried over magnesium sulfate and evaporated. The oily residue was allowed to stand at room temperature and the precipitating crystals were recrystallized from a mixture of benzene and n-hexane to give prisms of 2-[2-hydroxy-3-(o-tolyloxy)phenyl]acetic acid (1.10 g). mp 116°–117° C.

IR (Nujol): 3520, 1720, 1690 cm$^{-1}$.

N.M.R. (DMSO-d$_6$): δ2.23 (3H, s), 3.60 (2H, s), 6.50–7.43 (7H, m), 9.83 (1H, broad s).

Analysis for C$_{15}$H$_{14}$O$_4$: Calculated: C: 69.75, H: 5.46; Found: C: 69.81, H: 5.37.

EXAMPLE 4

(1) An aqueous solution (100 ml) of potassium hydroxide (17.0 g) was added all at once to a mixture of 2-(2-chlorophenoxy)-6-allylphenol (22.0 g) and dimethyl sulfate (23.0 g) under cooling. The mixture was stirred at room temperature for 30 minutes and extracted with diethyl ether. The extract was washed with water 3 times, dried over magnesium sulfate and then evaporated. The oily residue was subjected to distillation under reduced pressure to give colorless oil of 2-chlorophenyl 2-methoxy-3-allylphenyl ether (22.0 g). bp 149° C./0.8 mmHg.

I.R. (Film): 1640, 1280, 1260, 1220 cm$^{-1}$.

N.M.R. (CDCl$_3$): δ3.33–3.50 (2H, m), 3.86 (3H, s), 4.26–5.10 (1H, m), 5.10–5.23 (1H, m), 5.70–6.36 (1H, m), 6.66–7.53 (7H, m).

(2) 2-Chlorophenyl 2-methoxy-3-allylphenyl ether (21.50 g) was added to methanol (100 ml) saturated with potassium hydroxide, and the mixture was treated in a similar manner to that of Example 3-(2) and recrystallized from methanol to give colorless crystals of 2- chlorophenyl 2-methoxy-3-(1-propenyl)phenyl ether (19.40 g). mp 61°–62° C.

I.R. (Nujol): 1280, 1260 cm$^{-1}$.

N.M.R. (CDCl$_3$): δ1.90 (3H, d, J=6 Hz), 3.86 (3H, s), 6.0–7.56 (9H, m).

(3) Ozone gas was introduced into a solution of 2-chlorophenyl 2-methoxy-3-(1-propenyl)phenyl ether (17.60 g) in a mixture of ethyl acetate (120 ml) and acetic acid (5 ml) at 5° C. for an hour. Thereafter, nitrogen gas was introduced to the reaction mixture to remove the excess of ozone gas, and then dimethyl thioether was added thereto. The mixture was washed with aqueous solution of sodium bicarbonate and water successively, dried over magnesium sulfate and then evaporated. The oily residue was dissolved in diethyl ether, washed with an aqueous solution of sodium bicarbonate, dried and then evaporated to give oily 2-methoxy-3-(2-chlorophenoxy)benzaldehyde (7.0 g).

I.R. (Film): 1690, 1270, 1250 cm$^{-1}$.

N.M.R. (CDCl$_3$): δ4.06 (3H, s), 6.80–7.68 (7H, m), 10.44 (1H, s).

(4) 2-Methoxy-3-(2-chlorophenoxy)benzaldehyde (7.0 g) and malonic acid (5.60 g) were dissolved in pyridine (60 ml). To the solution was added piperidine (0.6 ml) and the mixture was heated gradually to 80° C., while carbon dioxide was produced. Thereafter, the mixture was refluxed under heating for 30 minutes. After cooling, the reaction mixture was poured into water (300 ml), acidified with conc. hydrochloric acid and extracted with diethyl ether. The extract was washed with water, dried over magnesium sulfate and then evaporated. The crystalline residue (7.10 g) was recrystallized from diisopropyl ether to give 3-[2-methoxy-3-(2-chlorophenoxy)phenyl]acrylic acid (5.1 g). mp 145°–147° C.

I.R. (Nujol): 1690, 1620, 1290, 1210 cm$^{-1}$.

N.M.R. (DMSO-d$_6$): δ3.93 (3H, s), 6.65, 7.86 (2H, ABq, J=16 Hz), 6.90–7.70 (7H, m), 12.56 (1H, broad s).

(5) Palladium on carbon (500 mg) was added to a solution of 3-[2-methoxy-3-(2-chlorophenoxy)phenyl]acrylic acid (5.0 g) in dioxan (80 ml), and hydrogen gas (400 ml) was introduced into the mixture. After filtration, the filtrate was evaporated to give oily 3-[2-methoxy-3-(2-chlorophenoxy)phenyl]propionic acid (5.0 g).

I.R. (Film): 1700 cm$^{-1}$.

N.M.R. (CDCl$_3$): δ2.53–3.40 (4H, m), 3.96 (3H, s), 6.70–7.56 (7H, m).

(6) 3-[2-Methoxy-3-(2-chlorophenoxy)phenyl]propionic acid (5.0 g) was dissolved in a mixture of 48% hydriodic acid (30 ml) and acetic anhydride (15 ml). The mixture was treated in a similar manner to that of Example 1-(5) and recrystallized from a mixture of benzene and n-hexane to give colorless crystals of 3-[2-hydroxy-3-(2-chlorophenoxy)phenyl]propionic acid (2.0 g). mp 90°–92° C.

I.R. (Nujol): 3470, 1710, 1680 cm$^{-1}$.

N.M.R. (CDCl$_3$): δ2.60–3.23 (4H, m), 6.60–7.60 (7H, m).

Analysis for C$_{15}$H$_{13}$O$_4$Cl: Calculated: C: 61.54, H: 4.48, Cl: 12.11; Found: C: 61.92, H: 4.30, Cl: 12.03.

(7) Acetic anhydride (10 ml) was added to a solution of 3-[2-hydroxy-3-(2-chlorophenoxy)phenyl]propionic acid (5.0 g) in benzene (30 ml), and refluxed under heating for 1.5 hours. The reaction mixture was evaporated, and toluene was added to the residue and then evaporated again. The crystalline residue (4.30 g) was recrystallized from a mixture of ethyl acetate and n-hexane to give 8-(2-chlorophenoxy)chroman-2-one (3.9 g). mp 123°–125° C.

I.R. (Nujol): 1770 cm$^{-1}$.

N.M.R. (CDCl$_3$): δ2.60–3.08 (4H, m), 6.64–7.44 (7H, m).

Analysis for C$_{15}$H$_{11}$O$_3$Cl: Calculated: C: 65.56, H: 4.04, Cl: 12.90; Found: C: 65.83, H: 3.85, Cl: 12.97.

EXAMPLE 5

(1) 2-Methyl-6-(2-chlorophenoxy)aniline (4.7 g) was dissolved in a mixture of conc. hydrochloric acid (4 ml) and water (6 ml) under warming, and cooled to give a suspension of the hydrochloride. An aqueous solution (3 ml) of sodium nitrite (1.4 g) was added dropwise to the suspension with stirring at 5°–7° C. in 5 minutes, and the mixture was stirred at the same temperature for 15 minutes. To the solution was added 42% fluoroboric acid (46 ml), and the mixture was stirred at 5°–7° C. for 30 minutes. The resultant precipitates were collected by filtration, washed with water and diethyl ether and then dried in vacuo to give the diazonium salt (6.4 g), mp 130°–133° C. (dec.).

Acetic acid (30 ml) was added to the diazonium salt and refluxed under heating for 8 hours. The reaction mixture was evaporated, and the residue was dissolved in diethyl ether. The solution was washed with an aqueous solution of sodium bicarbonate and water, dried over magnesium sulfate and then evaporated. The residue was subjected to column chromatography on silica gel (60 g) and eluted with n-hexane and then with a mixture of benzene and n-hexane (2:3). From the former eluate was obtained 2-chlorophenyl 2-fluoro-3-methylphenyl ether (400 mg).

I.R. (Film): 1570, 1480, 1450, 1280, 1250, 1230, 1200, 1060, 750 cm$^{-1}$.

N.M.R. (CCl$_4$): δ2.21 (3H, s), 6.54–7.33 (7H, m) On the other hand, 6-(2-chlorophenoxy)-o-cresol (1.3 g) was obtained from the later eluate. I.R. (Film): 3525, 1480, 1270, 1230, 1200, 1060, 760 cm$^{-1}$.

N.M.R. (CCl$_4$): δ2.24 (3H, s), 5.58 (1H, s), 6.43–7.36 (7H, m).

(2) A mixture of 6-(2-chlorophenoxy)-o-cresol (0.3 g), acetic acid (5 ml) and acetic anhydride (5 ml) was refluxed under heating for 7 hours. The reaction mixture was evaporated, and the oily residue was dissolved in diethyl ether, washed with an aqueous solution of sodium bicarbonate, dried over magnesium sulfate and then evaporated to give oily 2-chlorophenyl 2-acetoxy-3-methylphenyl ether (0.4 g).

I.R. (Film): 1760, 1280, 1180 cm$^{-1}$.

N.M.R. (CCl$_4$): δ2.17 (3H, s), 2.20 (3H, s), 6.57–7.48 (7H, m).

(3) A mixture of 2-chlorophenyl 2-acetoxy-3-methylphenyl ether (17 g), N-bromosuccinimide (13 g) and 2,2'-azobisisobutyronitrile (1.7 g) in benzene (150 ml) was refluxed under heating for 3 hours. After cooling, the precipitate was filtered off. The filtrate was washed with water, aqueous sodium thiosulfate and water successively, dried over magnesium sulfate and then evaporated to give oily 2-chlorophenyl 2-acetoxy-3-bromomethylphenyl ether (22.4 g).

I.R. (Film): 1760, 1460, 1270, 1170 cm$^{-1}$

N.M.R. (CCl$_4$): δ2.30 (3H, s), 4.40 (2H, s), 6.67–7.55 (7H, m).

(4) Powdered sodium cyanide (3.65 g) was added to a solution of 2-chlorophenyl 2-acetoxy-3-bromomethylphenyl ether (22 g) in dimethylsulfoxide (80 ml) with stirring at room temperature, and the mixture was stirred at the same temperature for 10 minutes. Water (200 ml) was added to the reaction mixture and extracted with diethyl ether. The extract was washed with water, dried over magnesium sulfate and then evaporated to give oily 2-[2-acetoxy-3-(2-chlorophenoxy)phenyl]acetonitrile (19 g).

To the above substance was added acetic acid (50 ml) and conc. hydrochloric acid (50 ml), and the mixture was refluxed under heating for 2 hours. After cooling, the reaction mixture was evaporated, and the residue was dissolved in an aqueous solution of sodium bicarbonate under stirring. The solution was washed with diethyl ether, acidified with conc. hydrochloric acid and extracted with diethyl ether. The extract was washed with water, dried over magnesium sulfate and then evaporated. The residue was pulverized with n-hexane and recrystallized from a mixture of benzene and n-hexane to give 2-[2-hydroxy-3-(2-chlorophenoxy)phenyl]acetic acid (5.4 g). mp 103°–105° C.

I.R. (Nujol): 3470, 1710, 1480, 1250 cm$^{-1}$.

N.M.R. (CDCl$_3$): $\delta$3.79 (2H, s), 6.70–7.57 (7H, m), 8.50 (2H, broad s).

Analysis for $C_{14}H_{11}O_4Cl$: Calculated: C: 60.33, H: 3.98, Cl: 12.72; Found: C: 60.75, H: 3.93, Cl: 12.49.

(5) A mixture of 2-[2-hydroxy-3-(2-chlorophenoxy)phenyl]acetic acid (1.9 g), methyl iodide (2.3 g) and potassium carbonate (2.2 g) in acetone (40 ml) was refluxed under heating for 4.5 hrs. After cooling, the reaction mixture was filtered. The filtrate was evaporated, and the oily residue was dissolved in methanol (30 ml). To the solution was added potassium hydroxide (1 g), and the mixture was refluxed under heating for 30 minutes. After cooling, the reaction mixture was evaporated and the residue was dissolved in water. The aqueous solution was washed with diethyl ether, acidified with conc. hydrochloric acid and extracted with diethyl ether. The extract was washed with water, dried over magnesium sulfate and evaporated. The residue was recrystallized from a mixture of benzene and n-hexane to give 2-[2-methoxy-3-(2-chlorophenoxy)phenyl]acetic acid (1.35 g). mp 87°–92° C.

I.R. (Nujol): 1720, 1580, 1480, 1280, 1230, 750 cm$^{-1}$.

N.M.R. (CDCl$_3$): $\delta$3.80 (2H, s), 3.97 (3H, s), 6.72–7.57 (7H, m), 11.32 (1H, broad s).

Analysis for $C_{15}H_{13}O_4Cl$: Calculated: C: 61.55, H: 4.48, Cl: 12.11; Found: C: 62.38, H: 4.56, Cl: 11.85.

(6) A mixture of 2-[2-hydroxy-3-(2-chlorophenoxy)phenyl]acetic acid (1.9 g) and p-toluenesulfonic acid (0.5 g) in benzene 50 ml was treated in a similar manner to that of Example 1-(6), and the residue was recrystallized from a mixture of diethyl ether and n-hexane to give 7-(2-chlorophenoxy)-2,3-dihydrobenzofuran-2-one (1.2 g). mp 118°–120° C.

I.R. (Nujol): 1820, 1480, 1470, 1450, 1275, 1265, 870, 760 cm$^{-1}$.

N.M.R. (DMSO-d$_6$): $\delta$4.07 (2H, s), 6.88–7.73 (7H, m).

Analysis for $C_{14}H_9O_3Cl$: Calculated: C: 64.50, H: 3.48, Cl: 13.60; Found: C: 64.21, H: 3.44, Cl: 13.33.

EXAMPLE 6

(1) A mixture of 2-methyl-6-(4-chlorophenoxy)aniline (36 g) and conc. hydrochloric acid (33 ml) in water (200 ml) was stirred to give the hydrochloride. To the mixture was added dropwise an aqueous solution (15 ml) of sodium nitrite (11 g) under ice-cooling in 15 minutes, and the mixture was stirred at the same temperature for 30 minutes. 42% Fluoroboric acid (36 ml) was added dropwise to the above mixture under ice-cooling in 15 minutes and allowed to stand overnight. The resultant precipitate was obtained by filtration, washed with water and diethyl ether. Glacial acetic acid (500 ml) was added to the substance obtained above and refluxed under heating for 8 hrs. After cooling, the reaction mixture was evaporated, and water was added to the residue and extracted with n-hexane. The extract was washed with water, aqueous sodium bicarbonate and water successively and then evaporated. The residue was dissolved in 10% aqueous sodium hydroxide, washed with n-hexane, acidified with conc. hydrochloric acid and extracted with n-hexane. The extract was washed with water, dried over magnesium sulfate and evaporated to give oily 6-(4-chlorophenoxy)-o-cresol (10.5 g).

I.R. (Film): 3530, 1490, 1270, 1210, 1100 cm$^{-1}$.

N.M.R. (CCl$_4$): $\delta$2.28 (3H, s), 5.53 (1H, broad s), 6.58–7.28 (7H, m).

(2) An aqueous solution (25 ml) of potassium hydroxide (7.5 g) was added to a mixture of 6-(4-chlorophenoxy)-o-cresol (10.5 g) and dimethyl sulfate (8.6 ml) with stirring at room temperature, and refluxed under heating for an hour. After cooling, water was added to the reaction mixture and extracted with n-hexane. The extract was washed with water, dried over magnesium sulfate and evaporated to give oily 4-chlorophenyl 2-methoxy-3-methylphenyl ether (10.7 g).

I.R. (Film): 1480, 1280, 1270, 1250, 1220, 1090, 1000 cm$^{-1}$.

N.M.R. (CCl$_4$): $\delta$2.30 (3H, s), 3.79 (3H, s), 6.77–7.33 (7H, m).

(3) A mixture of 4-chlorophenyl 2-methoxy-3-methylphenyl ether (10.7 g), N-bromosuccinimide (8.3 g) and 2,2'-azobisisobutyronitrile (830 mg) in benzene (70 ml) was refluxed under heating for 2 hrs., and the reaction mixture was treated in a similar manner to that of Example 5-(3) to give oily 4-chlorophenyl 2-methoxy-3-bromomethylphenyl ether (14.9 g).

I.R. (Film): 1570, 1480, 1270, 1230, 1210, 1000 cm$^{-1}$.

N.M.R. (CCl$_4$): $\delta$3.91 (3H, s), 4.48 (2H, s), 6.76–7.24 (7H, m).

(4) A solution of 4-chlorophenyl 2-methoxy-3-bromomethylphenyl ether (14.9 g) in dimethyl sulfoxide (40 ml) and powdered sodium cyanide (2.3 g) were treated in a similar manner to that of Example 5-(4) to give oily 2-[2-methoxy-3-(4-chlorophenoxy)phenyl]acetonitrile (11.8 g).

I.R. (Film): 2250, 1480, 1470, 1290, 1230, 1010 cm$^{-1}$.

N.M.R. (CCl$_4$): $\delta$3.63 (2H, s), 3.85 (3H, s), 6.73–7.29 (7H, m).

(5) 2-[2-Methoxy-3-(4-chlorophenoxy)phenyl]acetonitrile (11.8 g), glacial acetic acid (50 ml) and conc. hydrochloric acid (25 ml) were treated in a similar manner to that of Example 5-(4) to give oily 2-[2-methoxy-3-(4-chlorophenoxy)phenyl]acetic acid (6.7 g).

I.R. (Film): 1700, 1480, 1280, 1220, 1010 cm$^{-1}$.

N.M.R. (DMSO-d$_6$): $\delta$3.59 (2H, s), 3.68 (3H, s), 6.79–7.42 (7H, m).

(6) 48% Hydriodic acid (40 ml) was added dropwise to a solution of 2-[2-methoxy-3-(4-chlorophenoxy)phenyl]acetic acid (6.7 g) in acetic anhydride (20 ml) with stirring under ice-cooling in 5 minutes, and the mixture was refluxed under heating for 20 minutes. The reaction mixture was poured into an ice-water containing a small amount of sodium hydrogen sulfite and allowed to stand. The precipitating crystals were collected by filtration, washed with water, dried and then recrystallized from a mixture of benzene and n-hexane to give 2-[2-hydroxy-3-(4-chlorophenoxy)phenyl]acetic acid (4.4 g). mp 100°–102° C.

I.R. (Nujol): 3450, 1700, 1490, 1470, 1280, 1240 cm$^{-1}$.

N.M.R. (DMSO-d$_6$): δ3.64 (2H, s), 6.64–7.50 (7H, m).

Analysis for C$_{14}$H$_{11}$O$_4$Cl: Calculated: C: 60.33, H: 3.98, Cl: 12.72; Found: C: 60.56, H: 3.79, Cl: 12.73.

(7) 2-[2-Hydroxy-3-(4-chlorophenoxy)phenyl]acetic acid (2 g) was dissolved in acetic anhydride (10 ml) under warming, and the reaction mixture was evaporated. The resultant crystals were recrystallized from an aqueous ethanol to give 7-(4-chlorophenoxy)-2,3-dihydrobenzofuran-2-one, mp 100°–102° C.

I.R. (Nujol): 1810, 1490, 1465, 1270, 1215, 1105, 1050, 880, 830 cm$^{-1}$.

N.M.R. (DMSO-d$_6$): δ4.00 (2H, s), 6.93–7.50 (7H, m).

Analysis for C$_{14}$H$_9$O$_3$Cl: Calculated: C: 64.50, H: 3.48, Cl: 13.60 Found: C: 64.61, H: 3.18, Cl: 13.43.

EXAMPLE 7

(1) A mixture of 2-methyl-6-(3-chlorophenoxy)aniline (40 g) and conc. hydrochloric acid (36 ml) in water (125 ml) was treated in a similar manner to that of Example 6-(1) to give oily 6-(3-chlorophenoxy)-o-cresol (13.9 g)

I.R. (Film): 3525, 1780, 1470, 1270, 1200 cm$^{-1}$

N.M.R. (CCl$_4$): δ2.33 (3H, s), 5.50 (1H, broad s), 6.67–7.37 (7H, m).

(2) An aqueous solution (40 ml) of sodium hydroxide (10 g) and a mixture of 6-(3-chlorophenoxy)-o-cresol (13.9 g) and dimethyl sulfate (11 ml) were treated in a similar manner to that of Example 6-(2) to give oily 3-chlorophenyl 2-methoxy-3-methylphenyl ether (14.6 g).

I.R. (Film): 1580, 1470, 1280, 1230 cm$^{-1}$.

N.M.R. (CCl$_4$): δ2.33 (3H, s), 3.80 (3H, s), 6.64–7.33 (7H, m).

(3) A mixture of 3-chlorophenyl 2-methoxy-3-methylphenyl ether (14.6 g), N-bromosuccinimide (11.3 g) and 2,2'-azobisisobutyronitrile (1.1 g) in benzene (100 ml) was treated in a similar manner to that of Example 6-(3) to give oily 3-chlorophenyl 2-methoxy-3-bromomethylphenyl ether (20 g).

I.R. (Film): 1580, 1470, 1280, 1240 cm$^{-1}$.

N.M.R. (CCl$_4$): δ3.96 (3H, s), 4.53 (2H, s) 6.67–7.38 (7H, m).

(4) A solution of 3-chlorophenyl 2-methoxy-3-bromomethylphenyl ether (20 g) in dimethyl sulfoxide (50 ml) and powdered sodium cyanide (3 g) were treated in a similar manner to that of Example 5-(4) to give oily 2-[2-methoxy-3-(3-chlorophenoxy)phenyl]acetonitrile (16.4 g).

I.R. (Film): 2250, 1580, 1480, 1470, 1280, 1220, 1010 cm$^{-1}$.

N.M.R. (CCl$_4$): δ3.69 (2H, s), 3.89 (3H, s), 6.69–7.37 (7H, m).

(5) 2-[2-Methoxy-3-(3-chlorophenoxy)phenyl]acetonitrile (16.4 g), glacial acetic acid (80 ml) and conc. hydrochloric acid (30 ml) were treated in a similar manner to that of Example 5-(4) to give oily 2-[2-methoxy-3-(3-chlorophenoxy)phenyl]acetic acid (10.1 g).

I.R. (Film): 1700, 1580, 1470, 1440, 1280, 1230, 1210 cm$^{-1}$.

N.M.R. (DMSO-d$_6$): δ3.70 (2H, s), 3.80 (3H, s), 6.83–7.55 (7H, m).

(6) A solution of 2-[2-methoxy-3-(3-chlorophenoxy)phenyl]acetic acid (10 g) in acetic anhydride (30 ml) and 48% hydriodic acid (60 ml) were treated in a similar manner to that of Example 6-(6) to give 2-[2-hydroxy-3-(3-chlorophenoxy)phenyl]acetic acid (4.6 g). mp 99°–102° C.

I.R. (Nujol): 3520, 1710, 1590, 1470, 1275, 1215 cm$^{-1}$.

N.M.R. (DMSO-d$_6$): δ5.80 (2H, s), 6.63–7.53 (7H, m)

Analysis for C$_{14}$H$_{11}$O$_4$Cl: Calculated: C: 60.33, H: 3.98, Cl: 12.72; Found: C: 60.82, H: 3.84, Cl: 12.60.

(7) A solution of 2-[2-hydroxy-3-(3-chlorophenoxy)phenyl]acetic acid (2 g) in acetic anhydride (10 ml) was treated in a similar manner to that of Example 6-(7) to give 7-(3-chlorophenoxy)-2,3-dihydrobenzofuran-2-one (1.65 g). mp 105°–106° C.

I.R. (Nujol): 1815, 1590, 1490, 1475, 1260, 1220, 1100, 890 cm$^{-1}$.

N.M.R. (DMSO-d$_6$): δ4.00 (2H, s), 6.87–7.57 (7H, m).

Analysis for C$_{14}$H$_9$O$_3$Cl: Calculated: C: 64.50, H: 3.48, Cl: 13.60; Found: C: 64.86, H: 3.16, Cl: 13.60.

EXAMPLE 8

(1) 2-Allyl-6-(o-tolyloxy)phenol (80 g), dimethyl sulfate (63 ml), potassium hydroxide (56 g) and water (200 ml) were treated in a similar manner to that of Example 4-(1) to give oily o-tolyl 2-methoxy-3-allylphenyl ether (78.6 g). bp 120°–135° C./0.7 mmHg.

I.R. (Film): 1490, 1480, 1470, 1280, 1230 cm$^{-1}$.

N.M.R. (CCl$_4$): δ2.33 (3H, s), 3.35–3.57 (2H, m), 3.87 (3H, s), 4.87–5.30 (2H, m), 5.61–6.33 (1H, m), 6.53–7.27 (7H, m).

(2) o-Tolyl 2-methoxy-3-allylphenyl ether (30 g) and a solution of potassium hydroxide (40 g) in methanol (150 ml) were treated in a similar manner to that of Example 4-(2) to give oily o-tolyl 2-methoxy-3-(1-propenyl)phenyl ether (30 g).

I.R. (Film): 1570, 1490, 1470, 1430, 1280, 1260, 1230, 1180, 1120, 1010, 750 cm$^{-1}$.

N.M.R. (CCl$_4$): δ1.85 (3H, d, J=6 Hz), 2.24 (3H, s), 3.73 (3H, s), 6.25 (1H, d, J=6 Hz), 6.40–7.15 (8H, m).

(3) Ozone gas was introduced to a solution of o-tolyl 2-methoxy-3-(1-propenyl)phenyl ether (30 g) in a mixture of ethyl acetate (200 ml) and glacial acetic acid (10 ml) with stirring under cooling for an hour. The reaction mixture was treated in a similar manner to that of Example 4-(3) to give oily 2-methoxy-3-(o-tolyloxy)benzaldehyde (28 g)

I.R. (Film): 1680, 1480, 1470, 1260, 1230, 750 cm$^{-1}$.

N.M.R. (CCl$_4$): δ2.33 (3H, s), 4.05 (3H, s), 6.60–7.60 (7H, m), 10.40 (1H, s).

(4) 2-Methoxy-3-(o-tolyloxy)benzaldehyde (28 g), malonic acid (24 g), pyridine (200 ml) and piperidine (2 ml) were treated in a similar manner to that of Example 4-(4), and the resultant crude product was crystallized with a mixture of benzene and n-hexane to give 3-[2-methoxy-3-(o-tolyloxy)phenyl]acrylic acid (17.5 g). mp 143°–146° C.

I.R. (Nujol): 1680, 1620, 1470, 1280, 1270, 1220 cm$^{-1}$.

N.M.R. (DMSO-d$_6$): δ2.33 (3H, s), 3.87 (3H, s), 6.64 (1H, d, J=16 Hz), 6.75–7.67 (7H, m), 7.92 (1H, d, J=16 Hz).

(5) Hydrogen gas was introduced to a mixture of 3-[2-methoxy-3-(o-tolyloxy)phenyl]acrylic acid (17 g), palladium on carbon (5%, 3.4 g) and a small amount of glacial acetic acid in dioxane (200 ml) with stirring. The reaction mixture was filtered, and the filtrate was evaporated. The residue was pulverized with n-hexane to give 3-[2-methoxy-3-(o-tolyloxy)phenyl]propionic acid (15.4 g). mp 71°–75° C.

I.R. (Nujol): 1700, 1480, 1470, 1290, 1230, 1000 cm$^{-1}$.

N.M.R. (CDCl$_3$): δ2.32 (3H, s), 2.52–3.20 (4H, m), 3.94 (3H, s), 6.54–7.37 (7H, m), 10.63 (1H, s).

(6) A solution of 3-[2-methoxy-3-(o-tolyloxy)phenyl]-propionic acid (15 g) in acetic anhydride (40 ml) was added dropwise to 48% hydriodic acid (80 ml) with stirring under ice-cooling in 5 minutes, and after removing methyl iodide, the mixture was refluxed under heating for 20 minutes. After cooling, the reaction mixture was evaporated, and water was added to the residue and extracted with diethyl ether. The extract was washed with water, dried over magnesium sulfate and evaporated. The residue was added to a mixture of benzene (50 ml) and acetic anhydride (30 ml) and refluxed under heating for an hour. After cooling, the mixture was evaporated, and the residue was dissolved in diethyl ether, washed with water, aqueous sodium hydroxide and water successively, dried and then evaporated. The oily residue (13.8 g) was pulverized with n-hexane to give 8-(o-tolyloxy)chroman-2-one (11.4 g). This substance was purified by recrystallization from a mixture of ethanol and n-hexane. mp 80°–82° C.

I.R. (Nujol): 1760, 1475, 1265, 1220, 1200, 1140 cm$^{-1}$.

N.M.R. (CDCl$_3$): δ2.30 (3H, s), 2.63–3.23 (4H, m), 6.57–7.33 (7H, m).

Analysis for C$_{16}$H$_{14}$O$_3$: Calculated: C: 75.57, H: 5.55; Found: C: 75.20, H: 5.40.

(7) A mixture of 8-(o-tolyloxy)chroman-2-one (5.4 g) and potassium hydroxide (2 g) in methanol (50 ml) was refluxed under heating for 30 minutes. After cooling, the reaction mixture was evaporated, and the oily residue was dissolved in water, washed with diethyl ether, acidified with conc. hydrochloric acid and then extracted with diethyl ether. The extract was washed with water, dried over magnesium sulfate and evaporated. The residue was recrystallized twice from a mixture of ethyl acetate and n-hexane to give 3-[2-hydroxy-3-(o-tolyloxy)phenyl]propionic acid (1.0 g). mp 106°–107° C.

I.R. (Nujol): 3500, 1710, 1680, 1480, 1470, 1260, 1220, 1180, 750, 740 cm$^{-1}$.

N.M.R. (CDCl$_3$): δ2.23 (3H, s), 2.55–3.20 (4H, m), 6.40–7.35 (7H, m).

Analysis for C$_{16}$H$_{16}$O$_4$: Calculated: C: 70.57, H: 5.92; Found: C: 70.95, H: 6.01.

EXAMPLE 9

(1) A solution of 2-[2-methoxy-3-(o-tolyloxy)phenyl]acetonitrile (5.2 g) in dimethylformamide (10 ml) was added dropwise to a mixture of 50% sodium hydride (1.1 g) and dimethylformamide (20 ml) below 7° C. in 10 minutes and stirred at the same temperature for 30 minutes. Methyl iodide (6.2 g) was added dropwise to the mixture below 7° C. in 15 minutes and stirred at the same temperature for an hour. Chilled water (200 ml) was added to the reaction mixture, and the mixture was extracted with diethyl ether. The extract was washed with water, aqueous sodium hydrogen sulfite and water successively, dried over magnesium sulfate and then evaporated to give oily 2-[2-methoxy-3-(o-tolyloxy)-phenyl]-2,2-dimethylacetonitrile (5.7 g).

I.R. (Film): 2240, 1470, 1270, 1000 cm$^{-1}$.

N.M.R. (CCl$_4$): δ1.80 (6H, s), 2.33 (3H, s), 4.07 (3H, s), 6.60–7.33 (7H, m).

(2) Conc. hydrochloric acid (20 ml) and acetic acid (60 ml) were added to 2-[2-methoxy-3-(o-tolyloxy)-phenyl]-2,2-dimethylacetonitrile (5.7 g), and the mixture was refluxed under heating for 48 hours. After cooling, the reaction mixture was evaporated. Saturated aqueous solution of sodium bicarbonate (100 ml) was added to the oily residue and warmed. After cooling, the mixture was extracted with ethyl acetate, and the extract was washed with water, dried and evaporated. The solid residue was purified by recrystallization from a mixture of ethanol and n-hexane to give 3,3-dimethyl-7-(o-tolyloxy)-2,3-dihydrobenzofuran-2-one (2.5 g). mp 115°–117° C.

I.R. (Nujol): 1800, 1460, 1250, 1050 cm$^{-1}$.

N.M.R. (DMSO-d$_6$): δ1.51 (6H, s), 2.28 (3H, s), 6.77–7.47 (7H, m).

Analysis for C$_{17}$H$_{16}$O$_3$: Calculated: C: 76.10, H: 6.01; Found: C: 76.25, H: 6.01.

EXAMPLE 10

(1) A solution of 2-methoxy-3-(2-chlorophenoxy)benzaldehyde (5.0 g) in methanol (50 ml) and sodium borohydride (720 mg) were treated in a similar manner to that of Example 3-(5). The resultant residue was subjected to column chromatography on silica gel (100 g) and eluted with a mixture of benzene and ethyl acetate (10:1) to give crystalline 2-methoxy-3-(2-chlorophenoxy)benzyl alcohol (2.8 g).

I.R. (Film): 3400, 1480, 1280, 1240 cm$^{-1}$.

N.M.R. (CCl$_4$): δ3.92 (4H, s), 4.65 (2H, s), 6.65–7.50 (7H, m).

(2) A mixture of 2-methoxy-3-(2-chlorophenoxy)benzyl alcohol (5.5 g), thionyl chloride (3 ml) and pyridine (one drop) in benzene (40 ml) was treated in a similar manner to that of Example 3-(6) to give oily 2-chlorophenyl 2-methoxy-3-chloromethylphenyl ether (6.4 g).

I.R. (Film): 1480, 1280, 1230 cm$^{-1}$

N.M.R. (CCl$_4$): δ3.96 (3H, s), 4.57 (2H, s), 6.63–7.47 (7H, m).

(3) A solution of 2-chlorophenyl 2-methoxy-3-chloromethylphenyl ether (6.3 g) in dimethyl sulfoxide (40 ml) and powdered potassium cyanide (1.55 g) were treated in a similar manner to that of Example 3-(7) to give oily 2-[2-methoxy-3-(2-chlorophenoxy)phenyl]acetonitrile (6.0 g).

I.R. (Film): 2250, 1480, 1280, 1230 cm$^{-1}$.

N.M.R. (CCl$_4$): δ3.64 (2H, s), 3.95 (3H, s), 6.65–7.45 (7H, m).

(4) A mixture of 2-[2-methoxy-3-(2-chlorophenoxy)-phenyl]acetonitrile (6.0 g) and diethyl carbonate (10 g) in toluene (50 ml) was added to sodium ethoxide obtained from sodium metal (530 mg) and ethanol (20 ml), and the mixture was refluxed under heating for 2 hours. After cooling, the reaction mixture was poured into a mixture of water (60 ml) and acetic acid (60 ml). The organic layer was separated, and the aqueous layer was extracted with benzene. The organic layer and the benzene extract were combined, washed with water, aqueous sodium bicarbonate and water successively, dried over magnesium sulfate, treated with activated charcoal and then evaporated to give oily ethyl 2-cyano-2-[2-methoxy-3-(2-chlorophenoxy)phenyl]acetate (5.6 g).

I.R. (Film): 2250, 1740, 1480, 1270, 1230 cm$^{-1}$.

N.M.R. (CCl$_4$): δ1.30 (3H, t, J=7 Hz), 4.00 (3H, s), 4.24 (2H, q, J=7 Hz), 5.00 (1H, s), 6.70–7.53 (7H, m).

(5) 50% Sodium hydride (810 mg) was washed with petroleum ether twice and added to dried dimethyl formamide (50 ml). To the mixture was added dropwise a solution of ethyl 2-cyano-2-[2-methoxy-3-(2-chlorophenoxy)phenyl]acetate (5.3 g) in dimethyl formamide (10 ml) below 5° C. in 5 minutes, and the mixture was stirred at the same temperature for 20 minutes. To the mixture was added dropwise methyl iodide (3.3 g)

below 5° C. in 5 minutes, and the mixture was stirred at the same temperature for 30 minutes and then at room temperature for 30 minutes. The reaction mixture was poured into ice-water (300 ml), saturated with sodium chloride and extracted with diethyl ether. The extract was washed with aqueous sodium hydrogen sulfite and water, dried over magnesium sulfate and then evaporated to give oily ethyl 2-cyano-2-[2-methoxy-3-(2-chlorophenoxy)phenyl]propionate (5.8 g).

I.R. (Film): 2250, 1740, 1570, 1480, 1270, 1230 cm$^{-1}$.

N.M.R. (CCl$_4$): δ1.27 (3H, t, J=7 Hz), 1.85 (3H, s), 3.90 (3H, s), 4.20 (2H, q, J=7 Hz), 6.60-7.47 (7H, m).

(6) A mixture of ethyl 2-cyano-2-[2-methoxy-3-(2-chlorophenoxy)phenyl]propionate (5.8 g), conc. hydrochloric acid (20 ml) and acetic acid (40 ml) was refluxed under heating for 26 hours. After cooling, the reaction mixture was evaporated, and water was added to the residue. The mixture was evaporated again, and the oily residue was dissolved in saturated aqueous sodium bicarbonate under warming. After cooling, the aqueous solution was washed with diethyl ether, acidified with conc. hydrochloric acid and extracted with diethyl ether. The extract was washed with water, dried and then evaporated to give oily 2-[2-methoxy-3-(2-chlorophenoxy)phenyl]propionic acid (2.7 g).

I.R. (Film): 1700, 1570, 1470, 1230, 750 cm$^{-1}$.

N.M.R. (CDCl$_3$): δ1.49 (3H, d, J=7 Hz), 3.90 (3H, s), 4.15 (1H, q, J=7 Hz), 6.70-7.53 (7H, m).

(7) Hydriodic acid (55-58%, 20 ml) was added to a solution of 2-[2-methoxy-3-(2-chlorophenoxy)phenyl]propionic acid (2.7 g) in acetic anhydride (10 ml) under ice-cooling. The mixture was refluxed under heating for 30 minutes. The reaction mixture was poured into aqueous solution of sodium hydrogen sulfite and extracted with diethyl ether. The extract was washed with aqueous sodium hydrogen sulfite and water, dried and evaporated. To the oily residue was added acetic anhydride (10 ml), and the mixture was refluxed under heating for 30 minutes. After cooling, the mixture was evaporated, and the oily residue was dissolved in diethyl ether. The solution was washed with saturated aqueous sodium bicarbonate and water, dried and then evaporated. The residue was subjected to column chromatography on silica gel (40 g) and eluted with benzene, and the eluate was evaporated. The oily residue was crystallized with n-hexane to give 3-methyl-7-(2-chlorophenoxy)-2,3-dihydrobenzofuran-2-one (1.15 g). mp 92°-95° C.

I.R. (Nujol): 1790, 1470, 1460, 1110 cm$^{-1}$.

N.M.R. (DMSO-d$_6$): δ1.54 (3H, d, J=7 Hz), 4.17 (1H, q, J=7 Hz), 6.90-7.76 (7H, m).

EXAMPLE 11

(1) A mixture of sodium ethoxide prepared from ethanol (20 ml) and sodium metal (480 mg), 2-[2-methoxy-3-(o-tolyloxy)phenyl]acetonitrile (5 g) and diethyl carbonate (9.4 g) in toluene (50 ml) was treated in a similar manner to that of Example 10-(4) to give oily ethyl 2-cyano-2-[2-methoxy-3-(o-tolyloxy)phenyl]acetate (6.2 g).

I.R. (Film): 2250, 1740, 1480, 1470, 1270, 1230 cm$^{-1}$.

N.M.R. (CCl$_4$): δ1.28 (3H, t, J=7 Hz), 2.27 (3H, s), 3.90 (3H, s), 4.20 (2H, q, J=7 Hz), 4.90 (1H, s), 6.60-7.23 (7H, m).

(2) Sodium hydride (50%, 1 g), ethyl 2-cyano-2-[2-methoxy-3-(o-tolyloxy)phenyl]acetate (6.2 g) and methyl iodide (4.1 g) were treated in a similar manner to that of Example 10-(5) to give oily ethyl 2-cyano-2-[2-methoxy-3-(o-tolyloxy)phenyl]propionate (6.1 g).

I.R. (Film): 2250, 1750, 1490, 1470, 1280, 1230 cm$^{-1}$.

N.M.R. (CCl$_4$): δ1.27 (3H, t, J=7 Hz), 1.85 (3H, s), 2.27 (3H, s), 3.90 (3H, s), 4.20 (2H, q, J=7 Hz), 6.57-7.23 (7H, m).

(3) A mixture of ethyl 2-cyano-2-[2-methoxy-3-(o-tolyloxy)phenyl]propionate (6.1 g), conc. hydrochloric acid (20 ml) and acetic acid (40 ml) was refluxed under heating for 48 hours. The reaction mixture was treated in a similar manner to that of Example 10-(6) to give oily 2-[2-methoxy-3-(o-tolyloxy)phenyl]propionic acid (2.9 g).

I.R. (Film): 1700, 1490, 1470, 1270, 1230 cm$^{-1}$.

N.M.R. (DMSO-d$_6$): δ1.30 (3H, d, J=7 Hz), 2.20 (3H, s), 3.77 (3H, s), 3.94 (1H, q, J=7 Hz), 6.37-7.23 (7H, m), 9.08 (1H, broad s).

(4) A solution of 2-[2-methoxy-3-(o-tolyloxy)phenyl]propionic acid (2.9 g) in acetic anhydride (10 ml), hydroiodic acid (55-58%, 20 ml) and acetic anhydride (20 ml) were treated in a similar manner to that of Example 10-(7) to give 3-methyl-7-(o-tolyloxy)-2,3-dihydrobenzofuran-2-one (1.4 g). mp 45°-46° C.

I.R. (Nujol): 1800, 1480, 1450, 1250, 1120, 870 cm$^{-1}$.

N.M.R. (CDCl$_3$): δ1.57 (3H, d, J=8 Hz), 2.27 (3H, s), 3.76 (1H, q, J=8 Hz), 6.63-7.33 (7H, m).

Analysis for C$_{16}$H$_{14}$O$_3$: Calculated: C: 75.57, H: 5.55; Found: C: 75.70, H: 5.42.

EXAMPLE 12

(1) Ammonium chloride (17.1 g) was added to a solution of sodium cyanide (90% purity, 17.5 g) in water (110 ml), and the mixture was stirred at room temperature for 10 minutes. To the solution was added a solution of 2-methoxy-3-(o-tolyloxy)benzaldehyde (50.3 g) in dioxane (50 ml), and the mixture was stirred at room temperature for 2 hours. Water was poured into the reaction mixture and extracted with diethyl ether. The extract was evaporated, and acetic acid (125 ml) and conc. hydrochloric acid (250 ml) were added to the residue. The mixture was refluxed under heating for 4 hours, and acetic acid was distilled off. Water was added to the residue, washed with diethyl ether and adjusted to pH 6.0 with aqueous ammonium hydroxide. The precipitating crystals were collected by filtration, washed with water and dried to give 2-[2-methoxy-3-(o-tolyloxy)phenyl]glycine (22.5 g). mp 169°-170° C.

I.R. (Nujol): 3330, 3150, 2730, 2620, 1690, 1600, 1480, 1470, 1400, 1360, 1320, 1270, 1240 cm$^{-1}$.

N.M.R. (DMSO-d$_6$+D$_2$O): δ2.17 (3H, s), 3.77 (3H, s), 4.50 (1H, s), 6.50-7.35 (7H, m).

(2) 2-[2-Methoxy-3-(o-tolyloxy)phenyl]glycine (22.4 g) was added to a mixture of acetic anhydride (75 ml) and hydriodic acid (55-58%, 150 ml), and the mixture was refluxed under heating for 9 hours. The reaction mixture was poured into water (1 l) and adjusted to pH 12 with 20% aqueous sodium hydroxide. The solution was washed with diethyl ether and adjusted to pH 6.0 with conc. hydrochloric acid. The precipitating crystals were collected by filtration washed with water and dried to give 2-[2-hydroxy-3-(o-tolyloxy)phenyl]glycine (1500 g). mp 170°-173° C.

I.R. (Nujol): 3540, 1660, 1605, 1480, 1390, 1370, 1270, 1230 cm$^{-1}$.

N.M.R. (DMSO-d$_6$): δ2.27 (3H, s), 4.70 (1H, s), 6.43-7.37 (7H, m).

Analysis for C$_{15}$H$_{15}$NO$_4$: Calculated: C: 65.92, H: 5.53, N: 5.13; Found: C: 65.53, H: 5.37, N: 4.96.

(3) A mixture of 2-[2-hydroxy-3-(o-tolyloxy)phenyl]glycine (10.6 g) and phthalic anhydride (5.7 g)

was heated in an oil bath (200° C.) for 5 minutes. After cooling, the reaction mixture was subjected to column chromatography on silica gel (280 g) and eluted with benzene to give 3-phthalimido-7-(o-tolyloxy)-2,3-dihydrobenzofuran-2-one (1.8 g). mp 168°–170° C.

I.R. (Nujol): 1820, 1775, 1730, 1630, 1590, 1490, 1460, 1390, 1330 cm$^{-1}$.

N.M.R. (DMSO-d$_6$): δ2.30 (3H, s), 6.47 (1H, s), 6.80–7.53 (7H, m), 7.90 (4H, s)

Analysis for C$_{23}$H$_{15}$NO$_5$: Calculated: C: 71.68, H: 3.92, N: 3.64; Found: C: 71.80, H: 3.64, N: 3.59.

EXAMPLE 13

(1) Sodium hydride (50%, 650 mg), ethyl 2-cyano-2-[2-methoxy-3-(o-tolyloxy)phenyl]acetate (4 g) and ethyl bromide (3.35 g) were treated in a similar manner to that of Example 10-(5) to give oily ethyl 2-cyano-2-[2-methoxy-3-(o-tolyloxy)phenyl]butyrate (4.3 g).

I.R. (Film): 2250, 1740, 1490, 1480, 1230 cm$^{-1}$.

N.M.R. (CCl$_4$): δ1.14 (3H, t, J=7 Hz), 1.37 (3H, t, J=7 Hz), 2.35 (2H, q, J=7 Hz), 2.37 (3H, s), 4.00 (3H, s), 4.33 (2H, q, J=7 Hz), 6.70–7.37 (7H, m).

(2) A mixture of ethyl 2-cyano-2-[2-methoxy-3-(o-tolyloxy)phenyl]butyrate (4.1 g), conc. hydrochloric acid (20 ml) and acetic acid (40 ml) was refluxed under heating for 48 hours. The reaction mixture was evaporated, and 10% aqueous sodium hydroxide and ethanol were added to the residue. The mixture was refluxed under heating for 30 minutes and then evaporated. Water was added to the residue, washed with diethyl ether, acidified with conc. hydrochloric acid and extracted with diethyl ether. The extract was washed with water, dried and evaporated to give oily 2-[2-methoxy-3-(o-tolyloxy)phenyl]butyric acid (2.2 g).

I.R. (Film): 1700, 1680, 1460, 1270, 1230, 1180, 1120 cm$^{-1}$.

(3) Hydriodic acid (55–58%, 20 ml) and a solution of 2-[2-methoxy-3-(o-tolyloxy)phenyl]butyric acid (2.2 g) in acetic anhydride (10 ml) were treated in a similar manner to that of Example 10-(7). The resultant product, i.e. 2-[2-hydroxy-3-(o-tolyloxy)phenyl]butyric acid was treated with acetic anhydride (20 ml) in a similar manner to that of Example 10-(7) to give 3-ethyl-7-(o-tolyloxy)-2,3-dihydrobenzofuran-2-one (650 mg). mp 44°–45° C.

I.R. (Nujol): 1800, 1480, 1450, 1260, 1120 cm$^{-1}$.

N.M.R. (DMSO-d$_6$): δ0.90 (3H, t, J=7 Hz), 1.80–2.27 (2H, m), 2.27 (3H, s), 4.10 (1H, t, J=6 Hz), 6.77–7.46 (7H, m).

Analysis for C$_{17}$H$_{16}$O$_3$: Calculated: C: 76.10, H: 6.01; Found: C: 75.74, H: 5.90.

EXAMPLE 14

(1) A solution of 2-methyl-6-(2-fluorophenoxy)aniline (27 g) in a mixture of conc. hydrochloric acid (26 ml) and water (85 ml), aqueous solution (15 ml) of sodium nitrite (8.6 g) and 42% fluoroboric acid (27 ml) were treated in a similar manner to that of Example 5-(1). To the resultant diazonium salt was added glacial acetic acid (500 ml), and the mixture was refluxed under heating for 6 hours. After cooling, the reaction mixture was evaporated, and water was added to the residue. The mixture was extracted with n-hexane, and the extract was washed with water and saturated aqueous sodium bicarbonate, dried and evaporated. To the oily residue were added 20% aqueous sodium hydroxide and ethanol, and the mixture was refluxed under heating for an hour, and then evaporated. Water was added to the residue, washed with n-hexane, acidified with conc. hydrochloric acid and extracted with n-hexane. The extract was washed with water, dried and evaporated. The residue was subjected to column chromatography on silica gel (220 g) and eluted with benzene to give oily 6-(2-fluorophenoxy)-o-cresol (13.6 g).

I.R. (Film): 3550, 1500, 1480, 1270, 1190 cm$^{-1}$.

N.M.R. (CCl$_4$): δ2.25 (3H, s), 5.57 (1H, s), 6.47–7.20 (7H, m).

(2) Aqueous solution (50 ml) of potassium hydroxide (10.4 g) was added portionwise to a mixture of 6-(2-fluorophenoxy)-o-cresol (13.5 g) and dimethyl sulfate (15.5 g) with stirring under ice-cooling, and the mixture was refluxed under heating for an hour. After cooling, the reaction mixture was extracted with n-hexane, and the extract was washed with 10% aqueous sodium hydroxide and water, dried and then evaporated. The residue was purified by column chromatography (silica gel, benzene.n-hexane) to give oily 2-fluorophenyl 2-methoxy-3-methylphenyl ether (11.6 g).

I.R. (Film): 1500, 1480, 1280, 1260 cm$^{-1}$.

N.M.R. (CCl$_4$): δ2.26 (3H, s), 3.80 (3H, s), 6.70–7.27 (7H, m).

(3) A mixture of 2-fluorophenyl 2-methoxy-3-methylphenyl ether (11.5 g), N-bromosuccinimide (9 g) and azobisisobutyronitrile (0.9 g) in benzene (100 ml) was treated in a similar manner to that of Example 5-(3) to give oily 2-fluorophenyl 2-methoxy-3-bromomethylphenyl ether (17.6 g).

I.R. (Film): 1500, 1480, 1280, 1270 cm$^{-1}$

N.M.R. (CCl$_4$): δ3.89 (3H, s), 4.38 (2H, s), 6.57–7.13 (7H, m).

(4) Powdered sodium cyanide (2.5 g) was added to a solution of 2-fluorophenyl 2-methoxy-3-bromomethylphenyl ether (17.6 g) in dimethyl sulfoxide (50 ml) with stirring at room temperature, and the reaction mixture was treated in a similar manner to that of Example 5-(4) to give oily 2-[2-methoxy-3-(2-fluorophenoxy)phenyl]acetonitrile (10.4 g).

I.R. (Film): 2260, 1500, 1490, 1480, 1290, 1270 cm$^{-1}$.

N.M.R. (CCl$_4$): δ3.65 (2H, s), 3.97 (3H, s), 6.67–7.25 (7H, m).

(5) A mixture of sodium ethoxide prepared from sodium metal (470 mg) and ethanol (20 ml), 2-[2-methoxy-3-(2-fluorophenoxy)phenyl]acetonitrile (5 g) and diethyl carbonate (9.2 g) in toluene (50 ml) was treated in a similar manner to that of Example 10-(4) to give oily ethyl 2-cyano-2-[2-methoxy-3-(2-fluorophenoxy)phenyl]acetate (7 g).

I.R. (Film): 2250, 1740, 1500, 1480, 1260 cm$^{-1}$.

N.M.R. (CCl$_4$): δ1.23 (3H, t, J=7 Hz), 3.90 (3H, s), 4.20 (2H, q, J=7 Hz), 4.93 (1H, s), 6.70–7.20 (7H, m).

(6) Sodium hydride (50%, 1 g), ethyl 2-cyano-2-[2-methoxy-3-(2-fluorophenoxy)phenyl]acetate (7 g) and methyl iodide (4.14 g) were treated in a similar manner to that of Example 10-(5) to give oily ethyl 2-cyano-2-[2-methoxy-3-(2-fluorophenoxy)phenyl]propionate (6.2 g).

I.R. (Film): 2250, 1740, 1500, 1480, 1280, 1260 cm$^{-1}$.

N.M.R. (CCl$_4$): δ1.23 (3H, t, J=7 Hz), 1.84 (3H, s), 3.90 (3H, s), 4.17 (2H, q, J=7 Hz), 6.62–7.23 (7H, m).

(7) A mixture of ethyl 2-cyano-2-[2-methoxy-3-(2-fluorophenoxy)phenyl]propionate (6.2 g) and potassium hydroxide (2.1 g) in a mixture of ethanol (60 ml) and water (30 ml) was refluxed under heating for 72 hours, and the reaction mixture was evaporated. Water was added to the residue, washed with diethyl ether, acidified with conc. hydrochloric acid and extracted with diethyl ether. The extract was washed with water, dried and then evaporated to give oily 2-[2-methoxy-3-(2-fluorophenoxy)phenyl]propionic acid (3.85 g).

I.R. (Film): 1700, 1580, 1500, 1470, 1270, 1200 cm$^{-1}$.

N.M.R. (CDCl$_3$): δ1.53 (3H, d, J=7 Hz), 3.96 (3H, s), 4.20 (4H, q, J=7 Hz), 6.72–7.27 (7H, m), 9.67 (1H, s).

(8) Hydriodic acid (55–58%, 30 ml) was added portionwise to a solution of 2-[2-methoxy-3-(2-fluorophenoxy)phenyl]propionic acid (3.8 g) in acetic anhydride (15 ml) with stirring under ice-cooling, and the mixture was refluxed under heating for 15 minutes. After cooling, the reaction mixture was poured into aqueous solution of sodium hydrogen sulfite and extracted with diethyl ether. The extract was washed with aqueous sodium hydrogen sulfite and water, dried and then evaporated. The residue was purified by column chromatography (silica gel, benzene) and crystallization from ethanol to give 3-methyl-7-(2-fluorophenoxy)-2,3-dihydrobenzofuran-2-one (1.95 g). mp 70°–71.5° C.

I.R. (Nujol): 1800, 1500, 1480, 1470, 1120 cm$^{-1}$

N.M.R. (DMSO-d$_6$): δ1.57 (3H, d, J=8 Hz), 4.17 (1H, q, J=8 Hz), 6.88–7.63 (7H, m).

Analysis for C$_{15}$H$_{11}$O$_3$F: Calculated: C: 69.76, H: 4.29; Found: C: 69.58, H: 4.32.

EXAMPLE 15

(1) Sodium hydride (50%, 920 mg), ethyl 2-cyano-2-[2-methoxy-3-(2-chlorophenoxy)phenyl]acetate (6 g) and ethyl bromide (2.84 g) were treated in a similar manner to that of Example 10-(5) to give oily ethyl 2-cyano-2-[2-methoxy-3-(2-chlorophenoxy)phenyl]butyrate (5.9 g).

I.R. (Film): 2250, 1740, 1480, 1270, 1230 cm$^{-1}$

N.M.R. (CCl$_4$): δ1.11 (3H, t, J=7 Hz), 1.31 (3H, t, J=7 Hz), 2.33 (2H, q, J=7 Hz), 3.94 (3H, s), 4.25 (2H, q, J=7 Hz), 6.63–7.54 (7H, m).

(2) A mixture of ethyl 2-cyano-2-[2-methoxy-3-(2-chlorophenoxy)phenyl]butyrate (5.9 g) and potassium hydroxide (4.5 g) in ethanol (80 ml) and water (40 ml) was treated in a similar manner to that of Example 14-(7). The resultant residue was washed with n-hexane and dried to give 2-[2-methoxy-3-(2-chlorophenoxy)phenyl]butyric acid (4.15 g).

I.R. (Nujol): 1700, 1480, 1270, 1240 cm$^{-1}$.

N.M.R. (DMSO-d$_6$): δ0.80 (3H, t, J=7 Hz), 1.40–2.15 (2H, m), 3.78 (3H, s), 3.80 (1H, t, J=7 Hz), 6.68–7.63 (7H, m).

(3) A solution of 2-[2-methoxy-3-(2-chlorophenoxy)phenyl]butyric acid (4.1 g) in acetic anhydride (10 ml) and hydriodic acid (55–58%, 20 ml) were treated in a similar manner to that of Example 10-(7). The resultant oily residue, i.e. 2-[2-hydroxy-3-(2-chlorophenoxy)phenyl]butyric acid was treated with acetic anhydride (10 ml) in a similar manner to that of Example 10-(7). The resultant crystalline residue was recrystallized from ethanol to give 3-ethyl-7-(2-chlorophenoxy)-2,3-dihydrobenzofuran-2-one (2.3 g). mp 78°–79° C.

I.R. (Nujol): 1800, 1480, 1460, 1260, 750 cm$^{-1}$.

N.M.R. (DMSO-d$_6$): δ0.88 (3H, t, J=7 Hz), 1.99 (2H, q.d, J=7 Hz, 6 Hz), 4.08 (1H, t, J=6 Hz), 6.80–7.66 (7H, m).

Analysis for C$_{16}$H$_{13}$O$_3$Cl: Calculated: C: 66.56, H: 4.54, Cl: 12.28; Found: C: 66.63, H: 4.47, Cl: 12.35.

Thus obtained 3-ethyl-7-(2-chlorophenoxy)-2,3-dihydrobenzofuran-2-one was hydrolyzed with potassium hydroxide in methanol. The reaction mixture was acidified and extracted with diethyl ether. The extract was evaporated, and the residue was crystallized from benzene to give 2-[2-hydroxy-3-(2-chlorophenoxy)phenyl]butyric acid. mp 143°–145° C.

I.R. (Nujol): 3520, 1690, 1470, 1270, 1230, 1200 cm$^{-1}$.

N.M.R. (DMSO-d$_6$): δ0.84 (3H, t, J=7 Hz), 1.20–2.37 (2H, m), 4.87 (1H, t, J=7 Hz), 6.50–7.60 (7H, m), 9.30 (1H, broad s).

EXAMPLE 16

(1) Sodium hydride (50%, 920 mg), ethyl 2-cyano-2-[2-methoxy-3-(2-chlorophenoxy)phenyl]acetate (6 g) and n-propyl bromide (3.2 g) were treated in a similar manner to that of Example 10-(5) to give oily ethyl 2-cyano-2-[2-methoxy-3-(2-chlorophenoxy)phenyl]valerate (7 g).

I.R. (Film): 2250, 1740, 1480, 1270, 1230 cm$^{-1}$.

N.M.R. (CCl$_4$): δ0.90–2.35 (4H, m), 1.13 (3H, t, J=7 Hz), 1.27 (3H, t, J=7 Hz), 3.90 (3H, s), 4.21 (2H, q, J=7 Hz), 6.58–7.47 (7H, m).

(2) A mixture of ethyl 2-cyano-2-[2-methoxy-3-(2-chlorophenoxy)phenyl]valerate (7 g) and potassium hydroxide (5 g) in ethanol (80 ml) and water (40 ml) was treated in a similar manner to that of Example 14-(7) to give oily 2-[2-methoxy-3-(2-chlorophenoxy)phenyl]valeric acid (3.8 g).

I.R. (Film): 1700, 1570, 1470, 1450, 1270, 1230 cm$^{-1}$.

N.M.R. (CCl$_4$): δ0.8–2.22 (4H, m), 1.13 (3H, t, J=7 Hz), 3.84 (3H, s), 3.93 (1H, t, J=7 Hz), 6.80–7.45 (7H, m), 9.51 (1H, s).

(3) A solution of 2-[2-methoxy-3-(2-chlorophenoxy)phenyl]valeric acid (3.8 g) in acetic anhydride (10 ml) and hydriodic acid (55–58%, 20 ml) were treated in a similar manner to that of Example 14-(8) to give 3-n-propyl-7-(2-chlorophenoxy)-2,3-dihydrobenzofuran-2-one (1.5 g). mp 51°–53° C.

I.R. (Nujol): 1800, 1470, 1460, 1440, 1260, 750 cm$^{-1}$.

N.M.R. (DMSO-d$_6$): δ0.90 (3H, t, J=6 Hz), 1.1–1.68 (2H, m), 1.8–2.17 (2H, m), 4.13 (1H, t, J=5 Hz), 6.83–7.69 (7H, m).

Analysis for C$_{17}$H$_{15}$O$_3$Cl: Calculated: C: 67.44, H: 4.99, Cl: 11.71; Found: C: 67.53, H: 4.80, Cl: 11.56.

EXAMPLE 17

(1) A mixture of 2-[2-methoxy-3-(2-fluorophenoxy)phenyl]acetonitrile (5 g) and potassium hydroxide (2.2 g) in ethanol (60 ml) and water (30 ml) was refluxed under heating for 20 hours, and the reaction mixture was evaporated. To the residue was added water, and the mixture was washed with diethyl ether, acidified with conc. hydrochloric acid and extracted with diethyl ether. The extract was washed with water, dried and then evaporated to give oily 2-[2-methoxy-3-(2-fluorophenoxy)phenyl]acetic acid (5.4 g).

I.R. (Film): 1710, 1500, 1480, 1470, 1280, 1260 cm$^{-1}$.

N.M.R. (CCl$_4$): δ3.67 (2H, s), 3.88 (3H, s), 6.70–7.27 (7H, m).

(2) A solution of 2-[2-methoxy-3-(2-fluorophenoxy)phenyl]acetic acid (5.4 g) in acetic anhydride (15 ml) and hydriodic acid (55–58%, 30 ml) were treated in a similar manner to that of Example 10-(7). The resultant oily residue, i.e. 2-[2-hydroxy-3-(2-fluorophenoxy)phenyl]acetic acid was treated with acetic anhydride (10 ml) in a similar manner to that of Example 10-(7). The resultant crystalline residue was recrystallized from ethanol to give 7-(2-fluorophenoxy)-2,3-dihydrobenzofuran-2-one (3 g). mp 82°–84° C.

I.R. (Nujol): 1800, 1500, 1480, 1460, 1290, 1110 cm$^{-1}$.

N.M.R. (DMSO-d$_6$): δ4.00 (2H, s), 6.82–7.49 (7H, m).

Analysis for $C_{14}H_9O_3F$: Calculated: C: 68.85, H: 3.71; Found: C: 68.88, H: 3.82.

EXAMPLE 18

(1) A solution of 2-methyl-6-phenoxyaniline (19.3 g) in a mixture of conc. hydrochloric acid (17 ml) and water (60 ml), aqueous solution (10 ml) of sodium nitrite (6.7 g) and 42% fluoroboric acid (19 ml) were treated in a similar manner to that of Example 14-(1). The resultant diazonium salt was treated with acetic acid (400 ml) in a similar manner to that of Example 14-(1) to give oily 6-phenoxy-o-cresol (7.5 g).

I.R. (Film): 3530, 1590, 1490, 1470, 1270, 1210 cm$^{-1}$.

N.M.R. (CCl$_4$): $\delta$2.30 (3H, s), 5.53 (1H, s), 6.58–7.40 (8H, m).

(2) A mixture of 6-phenoxy-o-cresol (7.5 g) and dimethyl sulfate (14 g) and aqueous solution (30 ml) of potassium hydroxide (10.5 g) were treated in a similar manner to that of Example 14-(2). The resultant residue was pulverized with ethanol to give phenyl 2-methoxy-3-methylphenyl ether (6 g). mp 52°–53° C.

I.R. (Nujol): 1490, 1470, 1280, 1250, 1210, 1010, 760 cm$^{-1}$.

N.M.R. (CCl$_4$): $\delta$2.25 (3H, s), 3.77 (3H, s), 6.72–7.37 (8H, m).

(3) A mixture of phenyl 2-methoxy-3-methylphenyl ether (6 g), N-bromosuccinimide (5.2 g) and azobisisobutyronitrile (500 mg) in dried benzene (60 ml) was treated in a similar manner to that of Example 14-(3) to give oily phenyl 2-methoxy-3-bromomethylphenyl ether (8.5 g).

I.R. (Film): 1480, 1280, 1240, 1210 cm$^{-1}$.

N.M.R. (CCl$_4$): $\delta$3.95 (3H, s), 4.53 (2H, s), 6.84–7.63 (8H, m).

(4) A solution of phenyl 2-methoxy-3-bromomethylphenyl ether (8.5 g) in dimethyl sulfoxide (30 ml) and powdered sodium cyanide (1.45 g) were treated in a similar manner to that of Example 14-(4) to give oily 2-(2-methoxy-3-phenoxyphenyl)acetonitrile (6.6 g).

I.R. (Film): 2250, 1580, 1480, 1470, 1280, 1220 cm$^{-1}$.

N.M.R. (CCl$_4$): $\delta$3.65 (2H, s), 3.94 (3H, s), 6.77–7.43 (8H, m).

(5) A mixture of 2-(2-methoxy-3-phenoxyphenyl)acetonitrile (2.5 g) and potassium hydroxide (2.3 g) in water (20 ml) and ethanol (40 ml) was treated in a similar manner to that of Example 17-(1) to give oily 2-(2-methoxy-3-phenoxyphenyl)acetic acid (2.1 g).

I.R. (Film): 1700, 1580, 1480, 1280, 1210 cm$^{-1}$.

N.M.R. (DMSO-d$_6$): $\delta$3.58 (2H, s), 3.70 (3H, s), 6.75–7.43 (8H, m).

(6) A solution of 2-(2-methoxy-3-phenoxyphenyl)acetic acid (2.1 g) in acetic anhydride (10 ml) and hydriodic acid (55–58%, 20 ml) were treated in a similar manner to that of Example 10-(7). To the resultant oily residue containing 2-(2-hydroxy-3-phenoxyphenyl)acetic acid was added acetic anhydride (5 ml), and the mixture was refluxed under heating for 30 minutes and then evaporated. The oily residue (1.5 g) was purified by column chromatography (silica gel, benzene) and crystallization from ethanol to give 7-phenoxy-2,3-dihydrobenzofuran-2-one (950 mg). mp 60°–61° C.

I.R. (Nujol): 1810, 1490, 1480, 1460, 1260, 1100 cm$^{-1}$.

N.M.R. (DMSO-d$_6$): $\delta$4.00 (2H, s), 6.87–7.50 (8H, m).

Analysis for $C_{14}H_{10}O_3$: Calculated: C: 74.33, H: 4.46; Found: C: 74.70, H: 4.45.

On the other hand, the ethanol mother liquid was evaporated, and the residue was hydrolized with potassium hydroxide in methanol to give 2-(2-hydroxy-3-phenoxyphenyl)acetic acid. mp 132°–135° C.

I.R. (Nujol): 3400, 1700, 1480, 1250, 1200 cm$^{-1}$.

N.M.R. (DMSO-d$_6$): $\delta$3.58 (2H, s), 6.75–7.55 (8H, m).

Analysis for $C_{14}H_{12}O_4$: Calculated: C: 68.84, H: 4.95; Found: C: 68.94, H: 4.96.

EXAMPLE 19

(1) 50% Sodium hydride (650 mg), ethyl 2-cyano-2-[2-methoxy-3-(o-tolyloxy)phenyl]acetate (4 g) and n-propyl bromide (3.8 g) were treated in a similar manner to that of Example 14-(6) to give oily ethyl 2-cyano-2-[2-methoxy-3-(o-tolyloxy)phenyl]valerate (4.7 g).

I.R. (Film): 2250, 1740, 1470, 1270, 1230 cm$^{-1}$.

N.M.R. (CCl$_4$): $\delta$0.90–2.13 (7H, m), 1.25 (3H, t, J=7 Hz), 2.27 (3H, s), 3.87 (3H, s), 4.20 (2H, q, J=7 Hz), 6.55–7.20 (7H, m).

(2) A mixture of ethyl 2-cyano-2-[2-methoxy-3-(o-tolyloxy)phenyl]valerate (4.6 g) and potassium hydroxide (3.5 g) in ethanol (50 ml) and water (25 ml) was treated in a similar manner to that of Example 14-(7) to give oily 2-[2-methoxy-3-(o-tolyloxy)phenyl]valeric acid (3.7 g).

I.R. (Film): 1710, 1470, 1280, 1230 cm$^{-1}$.

N.M.R. (CDCl$_3$): $\delta$0.77–2.10 (4H, m), 1.22 (3H, t, J=8 Hz), 2.33 (3H, s), 3.97 (3H, s), 4.13 (1H, t, J=8 Hz), 6.60–7.37 (7H, m), 8.00 (1H, s).

(3) Hydriodic acid (55–58%, 20 ml) was added portionwise to a solution of 2-[2-methoxy-3-(o-tolyloxy)phenyl]valeric acid (3.7 g) in acetic anhydride (10 ml) with stirring under ice-cooling, and the mixture was refluxed under heating for an hour. After cooling, the reaction mixture was evaporated. The oily residue was purified by column chromatography (silica gel, benzene) to give oily 3-n-propyl-7-(o-tolyloxy)-2,3-dihydrobenzofuran-2-one (2.1 g).

I.R. (Film): 1800, 1480, 1460, 1270, 1180, 1120 cm$^{-1}$.

N.M.R. (CCl$_4$): $\delta$0.79–2.43 (4H, m), 0.95 (3H, t, J=6 Hz), 2.27 (3H, s), 3.63 (1H, t, J=6 Hz), 6.47–7.27 (7H, m).

EXAMPLE 20

(1) A mixture of 4-(2-chlorophenoxy)phenol (15 g), allyl bromide (12.5 g) and potassium carbonate (14 g) in methyl isobutyl ketone (100 ml) was refluxed under heating for 3 hours. After cooling, the reaction mixture was filtered, and the filtrate was evaporated. The residue was dissolved in diethyl ether, washed with dil. aqueous sodium hydroxide and water, dried and evaporated. The oily residue was stirred in a oil bath at 230° C. for 2 hours and distilled to give 2-allyl-4-(2-chlorophenoxy)phenol (14.7 g). bp 189°–192° C./3 mmHg.

I.R. (Film): 3450, 1500, 1470, 1430, 1270, 1230, 1180, 1060 cm$^{-1}$.

N.M.R. (CCl$_4$): $\delta$3.21–3.36 (2H, m), 4.88–5.19 (2H, m), 5.08 (1H, s), 5.60–6.26 (1H, m), 6.65–7.44 (7H, m).

(2) A mixture of 2-allyl-4-(2-chlorophenoxy)phenol (14.5 g) and potassium hydroxide (20 g) in methanol (70 ml) was treated in a similar manner to that of Example 4-(2) to give oily 2-(1-propenyl)-4-(2-chlorophenoxy)phenol (14.5 g).

I.R. (Film): 3425, 1480, 1440, 1270, 1240 cm$^{-1}$.

N.M.R. (CCl$_4$): $\delta$1.95 (3H, d, J=6 Hz), 5.00 (1H, broad s), 5.87–6.50 (2H, m), 6.74–7.53 (7H, m).

(3) Ozone gas was introduced into a solution of 2-(1-propenyl)-4-(2-chlorophenoxy)phenol (14.5 g) in a mixture of acetic acid (10 ml) and ethyl acetate (150 ml) with stirring at 2°–7° C. for an hour. After removing of the excess of ozone gas and addition of aqueous solution of sodium dithionite, the organic layer was separated, washed with saturated aqueous sodium bicarbonate and water, dried and evaporated. The residue was purified by column chromatography (silical gel, benzene) to give oily 2-hydroxy-5-(2-chlorophenoxy)benzaldehyde (10.4 g).

I.R. (Film): 3050, 1650, 1470, 1260, 1250 cm$^{-1}$.

N.M.R. (CCl$_4$): δ6.83–7.50 (7H, m), 9.73 (1H, s), 10.67 (1H, s).

(4) An aqueous solution (30 ml) of potassium hydroxide (8.2 g) was added portionwise to a mixture of 2-hydroxy-5-(2-chlorophenoxy)benzaldehyde (10.4 g) and dimethyl sulfate (10.5 g) with stirring at room temperature, and the mixture was stirred at 70° C. for an hour. After cooling, the reaction mixture was extracted with diethyl ether, and the extract was washed with water, dried and evaporated. The residue was crystallized from methanol to give 2-methoxy-5-(2-chlorophenoxy)benzaldehyde (8 g). mp 65°–66° C.

I.R. (Nujol): 1680, 1490, 1480, 1270, 1240 cm$^{-1}$.

N.M.R. (CCl$_4$): δ3.90 (3H, s), 6.77–7.47 (7H, m), 10.30 (1H, s).

(5) A solution of 2-methoxy-5-(2-chlorophenoxy)benzaldehyde (8 g) in methanol (50 ml) and sodium borohydride (685 mg) were treated in a similar manner to that of Example 3-(5) to give oily 2-methoxy-5-(2-chlorophenoxy)benzyl alcohol (8 g).

I.R. (Film): 3380, 1490, 1470, 1450, 1270, 1240, 1040 cm$^{-1}$.

N.M.R. (CCl$_4$): δ2.60 (1H, s), 3.77 (3H, s), 4.50 (2H, s), 6.70–7.43 (7H, m).

(6) A mixture of 2-methoxy-5-(2-chlorophenoxy)benzyl alcohol (8 g), thionyl chloride (4.4 ml) and pyridine (3 drops) in dried benzene (60 ml) was treated in a similar manner to that of Example 3-(6) to give oily 2-chlorophenyl 3-chloromethyl-4-methoxyphenyl ether (8.5 g).

I.R. (Film): 1500, 1480, 1240 cm$^{-1}$.

N.M.R. (CCl$_4$): δ3.84 (3H, s), 4.52 (2H, s), 6.65–7.47 (7H, m).

(7) Powdered potassium cyanide (2.05 g) was added to a solution of 2-chlorophenyl 3-chloromethyl-4-methoxyphenyl ether (8.5 g) and sodium iodide (4.7 g) in dimethyl sulfoxide (50 ml) at room temperature and stirred at the same temperature for an hour and then at 70° C. for 40 minutes. The reaction mixture was treated in a similar manner to that of Example 3-(7) to give oily 2-[2-methoxy-5-(2-chlorophenoxy)phenyl]acetonitrile (4.7 g).

I.R. (Film): 2250, 1500, 1480, 1230 cm$^{-1}$.

N.M.R. (CDCl$_3$): δ3.64 (2H, s), 3.84 (3H, s), 6.75–7.55 (7H, m).

(8) A mixture of sodium ethoxide prepared from sodium metal (415 mg) and ethanol (20 ml), 2-[2-methoxy-5-(2-chlorophenoxy)phenyl]acetonitrile (4.7 g) and diethyl carbonate (7.8 g) in toluene (50 ml) was treated in a similar manner to that of Example 10-(4) to give oily ethyl 2-cyano-2-[2-methoxy-5-(2-chlorophenoxy)phenyl]acetate (5.7 g).

I.R. (Film): 2250, 1740, 1500, 1480, 1230 cm$^{-1}$

N.M.R. (CCl$_4$): δ1.18 (3H, t, J=7 Hz), 3.74 (3H, s), 4.15 (2H, q, J=7 Hz), 4.78 (1H, s), 6.57–7.40 (7H, m).

(9) Sodium hydride (65.5%, 665 mg), ethyl 2-cyano-2-[2-methoxy-5-(2-chlorophenoxy)phenyl]acetate (5.7 g) and methyl iodide (3.55 g) were treated in a similar manner to that of Example 10-(5) to give oily ethyl 2-cyano-2-[2-methoxy-5-(2-chlorophenoxy)phenyl]propionate (5.5 g).

I.R. (Film): 2250, 1740, 1680, 1500, 1480, 1450, 1240 cm$^{-1}$.

N.M.R. (CCl$_4$): δ1.25 (3H, t, J=7 Hz), 1.85 (3H, s), 3.82 (3H, s), 4.24 (2H, q, J=7 Hz), 6.88–7.55 (7H, m).

(10) A mixture of ethyl 2-cyano-2-[2-methoxy-5-(2-chlorophenoxy)phenyl]propionate (5.5 g) and potassium hydroxide (4.3 g) in water 40 ml and ethanol (80 ml) was treated in a similar manner to that of Example 14-(7) to give oily 2-[2-methoxy-5-(2-chlorophenoxy)phenyl]propionic acid (3.2 g).

I.R. (Film): 1700, 1490, 1470, 1420, 1240, 1210 cm$^{-1}$.

N.M.R. (DMSO-d$_6$): δ1.28 (3H, d, J=7 Hz), 3.77 (3H, s), 3.90 (1H, q, J=7 Hz), 6.72–7.63 (7H, m).

(11) A solution of 2-[2-methoxy-5-(2-chlorophenoxy)phenyl]propionic acid (3.2 g) in acetic anhydride (10 ml) and hydriodic acid (55–58%, 20 ml) were treated in a similar manner to that of Example 14-(8) to give oily 3-methyl-5-(2-chlorophenoxy)2,3-dihydrobenzofuran-2-one (2.1 g).

I.R. (Film): 1800, 1470, 1220, 1120, 1030 cm$^{-1}$.

N.M.R. (CCl$_4$): δ1.48 (3H, d, J=7 Hz), 3.58 (1H, q, J=7 Hz), 6.68–7.48 (7H, m).

EXAMPLE 21

(1) A mixture of 2-(2-chlorophenylthio)phenol (33 g), allyl bromide (25 g) and dried potassium carbonate (29 g) in methyl isobutyl ketone (200 ml) was refluxed under heating for 1.5 hours. After cooling to the ambient temperature, the reaction mixture was filtered, and the filtrate was evaporated under reduced pressure. The resultant oily residue was stirred at 230° C. for 3 hours and then distilled under reduced pressure to give oily 2-(2-chlorophenylthio)-6-allylphenol (32.2 g) bp 157°–162° C./0.7 mmHg.

IR (Film): 3430, 1450, 1440, 1240, 1030, 750 cm$^{-1}$.

NMR (CCl$_4$): δ3.40 (2H, d, J=6 Hz), 4.80–5.13 (2H, m), 5.60–6.27 (1H, m), 6.37 (1H, s), 6.33–7.33 (7H, m).

(2) A mixture of 2-(2-chlorophenylthio)-6-allylphenol (32 g) and potassium hydroxide (41 g) in methanol (140 ml) was stirred at 110° C., and methanol was distilled off under ordinal pressure. The remaining mixture was further stirred at 100° C. for an hour, cooled to the ambient temperature and then dissolved in water. The aqueous solution was acidified with conc. hydrochloric acid under ice-water cooling. The resultant oily substance was extracted with diethyl ether, and the extract was washed with water, dried over magnesium sulfate and then evaporated under reduced pressure to give oily 2-(2-chlorophenylthio)-6-(1-propenyl)phenol (31.5 g). This product was subjected to column chromatography on silica gel (450 g) and eluted with a mixture of benzene and n-hexane (1:10) to give the purified oily product (26.3 g).

IR (Film): 3430, 1450, 1440, 1240, 1210, 1030 cm$^{-1}$.

NMR (CCl$_4$): δ1.88 (3H, d, J=6 Hz), 5.63–7.50 (10H, m).

(3) Ozone gas was introduced into a solution of 2-(2-chlorophenylthio)-6-(1-propenyl)phenol (26 g) in a mixture of ethyl acetate (200 ml) and acetic acid (10 ml) at temperature below 0° C. with stirring for an hour. The precipitates were collected by filtration, washed with ethyl acetate and then dried to give 2-hydroxy-3-(2-chlorophenylthio)benzaldehyde (15.9 g), mp. 111°–112.5° C. The filtrate and washings were combined, washed with dil. aqueous sodium hydrogen sulfite, saturated aqueous sodium bicarbonate and water in turn, dried over magnesium sulfate and then evaporated under reduced pressure. The residue was washed with methanol and dried to give the same product (3.2 g). Total yield 19.1 g.

IR (Nujol): 1660, 1450, 1300, 1220, 750 cm$^{-1}$.

NMR (DMSO-d$_6$): δ6.87–7.97 (7H, m), 10.13 (1H, s), 11.43 (1H, s).

Analysis for C$_{13}$H$_9$O$_2$SCl: Calculated: C: 58.98, H: 3.43, S: 12.11, Cl: 13.39; Found: C: 59.14, H: 3.43, S: 12.58, Cl: 13.66.

(4) A mixture of 2-hydroxy-3-(2-chlorophenylthio)-benzaldehyde (19.3 g) and dimethyl sulfate (18.4 g) was stirred at room temperature. To the mixture was added dropwise an aqueous solution (50 ml) of potassium hydroxide (12.5 g) at temperature below 60° C., and then the mixture was stirred for an hour. The reaction mixture was cooled to the ambient temperature and insoluble substance was filtered off. The filtrate was extracted with diethyl ether, and the extract was washed with water, dried over magnesium sulfate and then evaporated under reduced pressure to give oily 2-methoxy-3-(2-chlorophenylthio)benzaldehyde (9.2 g).

IR (Film): 1680, 1580, 1460, 1250 cm$^{-1}$.

NMR (CCl$_4$): δ4.00 (3H, s), 7.10–7.80 (7H, m), 10.32 (1H, s).

(5) Sodium borohydride (550 mg) was added in 10 minutes to a solution of 2-methoxy-3-(2-chlorophenylthio)benzaldehyde (9.1 g) in methanol (50 ml) with stirring at temperature below 15° C. After stirring the mixture at room temperature for 30 minutes, methanol was distilled off under reduced pressure. The residue was dissolved in water, acidified with conc. hydrochloric acid and extracted with diethyl ether. The extract was washed with water, dried and then evaporated under reduced pressure to give oily 2-methoxy-3-(2-chlorophenylthio)benzyl alcohol (9 g).

IR (Film): 3350, 1460, 1430, 1240, 1010 cm$^{-1}$.

NMR (CCl$_4$): δ3.26 (1H, s), 3.78 (3H, s), 4.58 (2H, s), 6.85–7.48 (7H, m).

(6) A mixture of 2-methoxy-3-(2-chlorophenylthio)benzyl alcohol (9 g), thionyl chloride (4.6 ml) and pyridine (3 drops) in dried benzene (60 ml) was refluxed under heating for 30 minutes. The reaction mixture was cooled to the ambient temperature and evaporated under reduced pressure. The residue was dissolved in diethyl ether, and the solution was washed with water, saturated aqueous sodium bicarbonate and water in turn, dried over magnesium sulfate and then evaporated under reduced pressure to give oily 2-chlorophenyl 2-methoxy-3-chloromethylphenyl thioether (9.2 g).

IR (Film): 1460, 1450, 1420, 1260, 1230, 1000 cm$^{-1}$.

NMR (CCl$_4$): δ4.00 (3H, s), 4.68 (2H, s), 6.98–7.60 (7H, m).

(7) A mixture of 2-chlorophenyl 2-methoxy-3-chloromethylphenyl thioether (9.2 g) and sodium iodide (4.8 g) in dimethyl sulfoxide (50 ml) was stirred at room temperature. To the mixture was added powdered potassium cyanide (2.1 g) all at once, and the mixture was stirred at 70° C. for 3 hours. The reaction mixture was poured into ice-water and extracted with diethyl ether. The extract was washed with water, dried and then evaporated to give oily 2-[2-methoxy-3-(2-chlorophenylthio)phenyl]acetonitrile (8.9 g). This product was purified by column chromatography (silica gel 150 g, benzene) to give purified oily product (4.1 g).

IR (Film): 2250, 1470, 1450, 1430, 1000 cm$^{-1}$.

NMR (CCl$_4$): δ3.70 (2H, s), 3.90 (3H, s), 6.95–7.50 (7H, m).

(8) A mixture of 2-[2-methoxy-3-(2-chlorophenylthio)phenyl]acetonitrile (1.5 g) and potassium hydroxide (870 mg) in ethanol (40 ml) and water (20 ml) was refluxed under heating for 24 hours. The reaction mixture was evaporated under reduced pressure and the residue was dissolved in water. The aqueous solution was washed with diethyl ether, acidified with dil. hydrochloric acid and extracted with diethyl ether. The extract was washed with water, dried and then evaporated to give oily 2-[2-methoxy-3-(2-chlorophenylthio)phenyl]acetic acid (1.4 g).

IR (Film): 1700, 1450, 1420, 1230 cm$^{-1}$.

NMR (CCl$_4$): δ3.75 (2H, s), 3.92 (3H, s), 6.89–7.54 (7H, m), 11.94 (1H, s).

(9) Hydriodic acid (58%, 10 ml) was added dropwise to a solution of 2-[2-methoxy-3-(2-chlorophenylthio)phenyl]acetic acid (1.4 g) in acetic anhydride (5 ml), and the mixture was refluxed under heating for 15 minutes. After cooling, the reaction mixture was poured into an aqueous solution of sodium hydrogen sulfite. The mixture was extracted with diethyl ether, and the extract was washed with aqueous sodium hydrogen sulfite and water in turn, dried and then evaporated under reduced pressure. To the residue was added acetic anhydride (10 ml), and the mixture was refluxed under heating for 10 minutes, and then evaporated under reduced pressure to give crystalline 7-(2-chlorophenylthio)-2,3-dihydrobenzofuran-2-one (1.1 g). This product was recrystallized from ethanol to give the pure product (0.8 g), mp. 145°–146° C.

IR (Nujol): 1800, 1450, 1430, 1380, 1060 cm$^{-1}$.

NMR (DMSO-d$_6$): δ3.90 (2H, s), 6.73–7.87 (7H, m).

Analysis for C$_{14}$H$_9$O$_2$SCl: Calculated: C: 60.76, H: 3.28, S: 11.59, Cl: 12.81; Found: C: 60.86, H: 3.36, S: 11.59, Cl: 13.17.

(10) 7-(2-Chlorophenylthio)-2,3-dihydrobenzofuran-2-one (0.2 g) was added to a solution of potassium hydroxide in methanol, and the mixture was stirred under warming to give 2-[2-hydroxy-3-(2-chlorophenylthio)phenyl]acetic acid (0.2 g), mp. 91°–93° C.

IR (Nujol): 3400, 1700, 1690, 1450 cm$^{-1}$.

NMR (DMSO-d$_6$): δ3.60 (2H, s), 6.55–7.55 (7H, m).

Analysis for C$_{14}$H$_{11}$O$_3$SCl: Calculated: C: 57.04, H: 3.76, S: 10.88, Cl: 12.03; Found: C: 56.95, H: 3.79, S: 11.14, Cl: 12.18.

EXAMPLE 22

(1) Sodium metal (217 mg) was dissolved in dried ethanol (20 ml) at room temperature and then ethanol was distilled off under reduced pressure. To the residue was added a mixture of 2-[2-methoxy-3-(2-chlorophenylthio)phenyl]acetonitrile (2.6 g) and ethyl carbonate (4.1 g) in toluene (50 ml), and the mixture was refluxed under heating for an hour. After cooling, the reaction mixture was poured into 50% acetic acid. The organic layer was separated, washed with water, saturated aqueous sodium bicarbonate and water in turn, dried and then evaporated under reduced pressure to give oily ethyl 2-cyano-2-[2-methoxy-3-(2-chlorophenylthio)phenyl]acetate (3.3 g).

IR (Film): 2250, 1740, 1450, 1260 cm$^{-1}$.

NMR (CCl$_4$): 3.93 (3H, s), 4.15 (2H, q, J=7 Hz), 4.97 (1H, s), 6.88–7.42 (7H, m).

(2) A solution of ethyl 2-cyano-2-[2-methoxy-3-(2-chlorophenylthio)phenyl]acetate (3.2 g) in dimethylformamide (10 ml) was added dropwise to a mixture of sodium hydride (65%, 330 mg) and dimethylformamide (20 ml) in 10 minutes at temperature below 10° C. After stirring the mixture at the same temperature for 20 minutes, methyl iodide (2.5 g) was added to the mixture. The mixture was stirred at the same temperature for 15 minutes and then at room temperature for 20 minutes. The reaction mixture was poured into water and extracted with diethyl ether. The extract was washed with water, dried and then evaporated under reduced pressure to give oily ethyl 2-cyano-2-[2-methoxy-3-(2-chlorophenylthio)phenyl]propionate (3.4 g).

IR (Film): 2250, 1740, 1450, 1230 cm$^{-1}$.

NMR (CCl$_4$): $\delta$1.20 (3H, t, J=7 Hz), 1.81 (3H, s), 3.90 (3H, s), 4.15 (2H, q, J=7 Hz), 6.76-7.48 (7H, m).

(3) A mixture of ethyl 2-cyano-2-[2-methoxy-3-(2-chlorophenylthio)phenyl]propionate (3.3 g) and potassium hydroxide (1.5 g) in ethanol (60 ml) and water (30 ml) was refluxed under heating for 48 hours. After cooling, ethanol was distilled off from the reaction mixture. To the residue was added water, and the aqueous solution was washed with diethyl ether, acidified with conc. hydrochloric acid and extracted with diethyl ether. The extract was washed with water, dried and then evaporated under reduced pressure to give oily 2-[2-methoxy-3-(chlorophenylthio)phenyl]propionic acid (1.9 g).

IR (Film): 1700, 1450, 1420, 1230 cm$^{-1}$.

NMR (CCl$_4$): $\delta$1.45 (3H, d, J=8 Hz), 3.85 (3H, s), 4.09 (1H, q, J=8 Hz), 6.88-7.36 (7H, m).

(4) 2-[2-Methoxy-3-(2-chlorophenylthio)phenyl]propionic acid (1.9 g), acetic anhydride (5 ml) and hydriodic acid (58%, 10 ml) were treated in a similar manner to that of Example 21-(9) to give oily 3-methyl-7-(2-chlorophenylthio)-2,3-dihydrobenzofuran-2-one (1.4 g). This product was subjected to column chromatography (silica gel 30 g, benzene), and the resultant oily substance was crystallized with ethanol to give crystaline product (1.2 g), mp. 63°-64° C.

IR (Nujol): 1800, 1450, 1430, 1100 cm$^{-1}$.

NMR (CCl$_4$): $\delta$1.53 (3H, d, J=7 Hz), 3.68 (1H, q, J=7 Hz), 6.89-7.43 (7H, m).

Analysis for C$_{15}$H$_{11}$O$_2$SCl: Calculated: C: 61.96, H: 3.81, S: 11.03, Cl: 12.19; Found: C: 62.01, H: 3.65, S: 11.35, Cl: 12.24.

(5) 3-Methyl-7-(2-chlorophenylthio)-2,3-dihydrobenzofuran-2-one was treated with potassium hydroxide in the same manner as Example 21-(10) to give crystalline 2-[2-hydroxy-3-(2-chlorophenylthio)phenyl]propionic acid, mp. 143°-145° C.

IR (Nujol): 3425, 3400, 1710, 1690, 1460, 1450 cm$^{-1}$.

NMR (DMSO-d$_6$): $\delta$1.36 (3H, d, J=7 Hz), 4.01 (1H, q, J=7 Hz), 6.58-7.60 (7H, m).

Analysis for C$_{15}$H$_{13}$O$_3$SCl: Calculated: C: 58.34, H: 4.24, S: 10.39, Cl: 11.48; Found: C: 58.31, H: 4.21, S: 10.58, Cl: 11.25.

EXAMPLE 23

(1) To a suspension of 2-hydroxy-3-(2-chlorophenylthio)benzaldehyde (5.8 g) in methanol (50 ml) was added sodium borohydride (820 mg) at temperature below 15° C. with stirring. The mixture was treated in a similar manner to that of Example 21-(5) to give oily 2-hydroxy-3-(2-chlorophenylthio)benzyl alcohol (6 g). This oily substance was left to stand at room temperature to give crystals.

IR (Nujol): 3470, 3200, 1460, 1000 cm$^{-1}$.

NMR (DMSO-d$_6$): $\delta$4.63 (2H, s), 5.00 (1H, br. s), 6.63-7.57 (7H, m), 9.15 (1H, br. s).

(2) Dimethyl sulfate (5.7 g) was added to a mixture of 2-hydroxy-3-(2-chlorophenylthio)benzyl alcohol (6 g) and potassium hydroxide (3.8 g) in water (20 ml) in 10 minutes with stirring. The mixture was stirred at 50° C. for 1.5 hours, and the reaction mixture was treated in a similar manner to that of Example 21-(4) to give oily 2-methoxy-3-(2-chlorophenylthio)benzyl alcohol (6.1 g). This product was purified by column chromatography (silica gel 100 g, benzene-ethyl acetate 10:1) to give purified oily substance (5.6 g). This product was identified with the compound obtained in Example 21-(5) by IR and NMR spectrum.

EXAMPLE 24

(1) m-Chloroperbenzoic acid (7.5 g) was added to a solution of ethyl 2-cyano-2-[2-methoxy-3-(2-chlorophenylthio)phenyl]propionate (5 g) in methylene chloride (100 ml) in 30 minutes at room temperature, and the mixture was stirred at room temperature for 2 hours. The reaction mixture was washed with saturated aqueous sodium bicarbonate and water in turn, dried and then evaporated under reduced pressure. The oily residue was crystallized with ethyl acetate to give ethyl 2-cyano-2-[2-methoxy-3-(2-chlorobenzenesulfonyl)phenyl]propionate (3.8 g), mp. 178°-179° C.

IR (Nujol): 2250, 1730, 1460, 1310, 1170, 1140 cm$^{-1}$.

NMR (CDCl$_3$): $\delta$0.90 (3H, t, J=7 Hz), 1.97 (3H, s), 3.90 (2H, q, J=7 Hz), 3.97 (3H, s), 7.27-8.40 (7H, m).

(2) A solution of ethyl 2-cyano-2-[2-methoxy-3-(2-chlorobenzenesulfonyl)phenyl]propionate (3.6 g) in hydriodic acid (58%, 10 ml) and glacial acetic acid (30 ml) was refluxed under heating for 21 hours. After cooling, the reaction mixture was concentrated under reduced pressure. To the residue was added dil. aqueous sodium hydrogen sulfite, and the mixture was extracted with diethyl ether. The extract was washed with dil. aqueous sodium hydrogen sulfite and water in turn, dried and evaporated under reduced pressure. To the oily residue was added acetic anhydride (5 ml), and the mixture was refluxed under heating for 10 minutes and then evaporated under reduced pressure. The resultant residue was crystallized with ethanol to give 3-methyl-7-(2-chlorobenzenesulfonyl)-2,3-dihydrobenzofuran-2-one (2.2 g), mp. 94°-96° C.

IR (Nujol): 1820, 1450, 1440, 1330 cm$^{-1}$.

NMR (CDCl$_3$): $\delta$1.52 (3H, d, J=8 Hz), 3.68 (1H, q, J=8 Hz), 7.24-8.45 (7H, m).

Analysis for C$_{15}$H$_{11}$O$_4$SCl: Calculated: C: 55.82, H: 3.44, S: 9.94; Found: C: 55.51, H: 3.37, S: 10.15.

(3) 3-Methyl-7-(2-chlorobenzenesulfonyl)-2,3-dihydrobenzofuran-2-one was treated with potassium hydroxide in methanol in a similar manner to that of Example 21-(10) to give 2-[2-hydroxy-3-(2-chlorobenzenesulfonyl)phenyl]propionic acid, mp. 180°-181° C.

IR (Nujol): 3420, 1700, 1460, 1140 cm$^{-1}$.

NMR (DMSO-d$_6$): $\delta$1.33 (3H, d, J=7 Hz), 4.06 (1H, q, J=7 Hz), 6.97-8.42 (7H, m), 9.52 (2H, br. s).

Analysis for C$_{15}$H$_{13}$O$_5$SCl: Calculated: C: 52.87, H: 3.84, S: 9.41, Cl: 10.40; Found: C: 52.91, H: 3.88, S: 9.66, Cl: 10.31.

EXAMPLE 25

(1) Ethyl-2-cyano-2-[2-methoxy-3-(o-tolyloxy)phenyl]acetate (5 g), which was prepared from 2-(o-tolyloxy)-6-allylphenol according to the same processes as Examples 21-(2), (3), (4), (5), (6), (7) and 22-(1), was dissolved in dimethylformamide (10 ml). The solution was added dropwise to a suspension of sodium hydride (65%, 600 mg) in dimethylformamide (30 ml) in 10 minutes with stirring at temperature below 10° C., and the mixture was stirred at the same temperature for 30 minutes. To the mixture was added n-hexyl bromide (5 g) at room temperature. The mixture was stirred at 50° C. for an hour, poured into water and extracted with diethyl ether. The extract was washed with aqueous soldium hydrogen sulfite and water in turn, dried and then evaporated under reduced pressure to give oily ethyl 2-cyano-2-[2-methoxy-3-(o-tolyloxy)phenyl]-n-octanoate (6.6 g).

IR (Film): 2925, 1740, 1480, 1230 cm$^{-1}$.

NMR (CCl$_4$): $\delta$0.64–2.38 (13H, m), 1.23 (3H, t, J=7 Hz), 2.18 (3H, s), 3.80 (3H, s), 4.18 (2H, q, J=7 Hz), 6.47–7.20 (7H, m).

(2) A mixture of ethyl 2-cyano-2-[2-methoxy-3-(o-tolyloxy)phenyl]-n-octanoate (6.6 g), acetic acid (30 ml) and hydriodic acid (58%, 30 ml) was refluxed under heating for 48 hours. After cooling, acetic acid was distilled off under reduced pressure. To the residue was added water, and the mixture was extracted with diethyl ether. The extract was washed with water, aqueous sodium hydrogen sulfite, aqueous sodium bicarbonate and water in turn, dried and then evaporated under reduced pressure. The oily residue (4.5 g) was subjected to column chromatography on silica gel (80 g) and eluted with benzene to give oily 3-(n-hexyl)-7-(o-tolyloxy)-2,3-dihydrobenzofuran-2-one (2.5 g).

IR (Film): 2920, 1800, 1480, 1460, 1270, 1110 cm$^{-1}$.

NMR (CCl$_4$): $\delta$0.67–2.8 (13H, m), 3.65 (1H, t, J=6 Hz), 6.63–7.30 (7H, m).

Analysis for C$_{21}$H$_{24}$O$_3$: Calculated: C: 77.75, H: 7.46; Found: C: 77.76, H: 7.54.

This oily product was crystallized with ethanol to give solid substance of mp. 36+–37° C.

(3) 3-n-Hexyl-7-(o-tolyloxy)-2,3-dihydrobenzofuran-2-one was treated with potassium hydroxide in methanol in a similar manner to that of Example 21-(10) to give 2-[2-hydroxy-3-(o-tolyloxy)phenyl]n-octanoic acid, mp. 65°–66° C.

IR (Nujol): 3450, 3370, 1710, 1690, 1470, 1260 cm$^{-1}$.

NMR (DMSO-d$_6$): $\delta$0.66–2.13 (13H, m), 2.27 (3H, s), 3.97 (1H, t, J=7 Hz), 6.43–7.38 (7H, m), 9.17 (1H, br. s).

Analysis for C$_{21}$H$_{26}$O$_4$: Calculated: C: 73.66, H: 7.66; Found: C: 73.76, H: 7.81.

EXAMPLE 26

(1) A solution of ethyl 2-cyano-2-[2-methoxy-3-(o-tolyloxy)phenyl]acetate (5 g) in dimethylformamide (10 ml) was added dropwise to a suspension of sodium hydride (65%, 600 mg) in dimethylformamide (30 ml) in 10 minutes at temperature below 10° C. with stirring, and the mixture was stirred at the same temperature for 10 minutes. n-Pentyl chloride (3.3 g) was added to the mixture and stirred at 110° C. for 2 hours. The reaction mixture was treated in a similar manner to that of Example 25-(1) to give oily ethyl 2-cyano-2-[2-methoxy-3-(o-tolyloxy)phenyl]-n-heptanoate (5.9 g).

IR (Film): 2250, 1740, 1470, 1230 cm$^{-1}$.

NMR (CCl$_4$): $\delta$0.63–2.28 (11H, m), 1.27 (3H, t, J=7 Hz), 2.27 (3H, s), 3.88 (3H, s), 4.23 (2H, q, J=7 Hz), 6.54–7.30 (7H, m).

(2) A mixture of ethyl 2-cyano-2-[2-methoxy-3-(o-tolyloxy)phenyl]-n-heptanoate (5.9 g), hydriodic acid (58%, 10 ml) and acetic acid (20 ml) was refluxed under heating for 48 hours. The reaction mixture was poured into water and extracted with diethyl ether. The extract was washed with aqueous sodium hydrogen sulfite and water in turn, dried and evaporated under reduced pressure. To the oily residue was added acetic anhydride (5 ml), and the mixture was refluxed under heating for 10 minutes and then evaporated under reduced pressure. The resultant oily residue was purified by column chromatography (silica gel 80 g, benzene) to give oily 3-(n-pentyl)-7-(o-tolyloxy)-2,3-dihydrobenzofuran-2-one (2.5 g).

IR (Film): 1810, 1490, 1120 cm$^{-1}$.

NMR (CCl$_4$): $\delta$0.80–2.15 (11H, m), 2.27 (3H, s), 3.64 (1H, t, J=6 Hz), 6.60–7.28 (7H, m).

Analysis for C$_{20}$H$_{22}$O$_3$: Calculated: C: 77.39, H: 7.14; Found: C: 77.43, H: 6.98.

(3) 3-(n-Pentyl)-7-(o-tolyloxy)-2,3-dihydrobenzofuran-2-one was treated with potassium hydroxide in methanol in a similar manner to that of Example 21-(10) to give 2-[2-hydroxy-3-(o-tolyloxy)phenyl]n-heptanoic acid, mp. 113°–114° C.

IR (Nujol): 3500, 1700, 1470 cm$^{-1}$.

NMR (DMSO-d$_6$): $\delta$0.87–2.00 (11H, m), 2.28 (3H, s), 4.00 (1H, t, J=8 Hz), 6.47–7.40 (7H, m), 9.17 (1H, br. s).

Analysis for C$_{20}$H$_{24}$O$_4$: Calculated: C: 73.14, H: 7.37; Found: C: 72.98, H: 7.38.

EXAMPLE 27

(1) A suspension of sodium hydride (65%, 600 mg) in dimethylformamide (30 ml), a solution of ethyl 2-cyano-2-[2-methoxy-3-(o-tolyloxy)phenyl]acetate (5 g) in dimethylformamide (10 ml) and n-butyl iodide (5.7 g) were treated in a similar manner to that of Example 25-(1) to give oily ethyl 2-cyano-2-[2-methoxy-3-(o-tolyloxy)phenyl]n-hexanoate (6.5 g).

IR (Film): 2250, 1740, 1470, 1280, 1230 cm$^{-1}$

NMR (CCl$_4$): $\delta$0.74–2.47 (9H, m), 1.27 (3H, t, J=7 Hz), 2.30 (3H, s), 3.92 (3H, s), 4.25 (2H, q, J=7 Hz), 6.60–7.37 (7H, m).

(2) A mixture of ethyl 2-cyano-2-[2-methoxy-3-(o-tolyloxy)phenyl]-n-hexanoate (6.5 g), hydriodic acid (58%, 10 ml) and glacial acetic acid (20 ml) was refluxed under heating for 47 hours. After cooling, the reaction mixture was poured into dil. aqueous sodium hydrogen sulfite and extracted with diethyl ether. The extract was washed with water, dil. aqueous sodium hydrogen sulfite and water in turn, dried and evaporated under reduced pressure. To the oily residue was added acetic anhydride (10 ml), and the mixture was refluxed under heating for 10 minutes and evaporated under reduced pressure. Water and ethanol were added to the residue, and the mixture was concentrated under reduced pressure. The oily residue was purified by column chromatography (silica gel 80 g, benzene) to give 3-(n-butyl) 7-(o-tolyloxy)-2,3-dihydrobenzofuran-2-one (2.8 g).

IR (Film): 1810, 1490, 1260, 1120 cm$^{-1}$.

NMR (CCl$_4$): $\delta$0.85–2.15 (9H, m), 2.28 (3H, s), 3.64 (1H, t, J=6 Hz), 6.60–7.27 (7H, m).

Analysis for C$_{19}$H$_{20}$O$_3$: Calculated: C: 77.00, H: 6.80; Found: C: 77.16, H: 6.80.

(3) 3-(n-Butyl)-7-(o-tolyloxy)-2,3-dihydrobenzofuran-2-one was treated with potassium hydroxide in methanol in a similar manner to that of Example 21-(10) to give 2-[2-hydroxy-3-(o-tolyloxy)-phenyl]-n-hexanoic acid, mp. 83°–84° C.

IR (Nujol): 3460, 3400, 1700, 1680, 1470 cm$^{-1}$.

NMR (DMSO-d$_6$): $\delta$0.80–2.00 (9H, m), 2.23 (3H, s), 3.94 (1H, t, J=7 Hz), 6.43–7.37 (7H, m), 9.13 (1H, br. s).

Analysis for C$_{19}$H$_{22}$O$_4$: Calculated: C: 72.59, H: 7.05; Found: C: 72.49, H: 7.09.

EXAMPLE 28

(1) A suspension of sodium hydride (65%, 600 mg) in dimethylformamide (30 ml), a solution of ethyl 2-cyano-2-[2-methoxy-3-(o-tolyloxy)phenyl]acetate (5 g) in dimethylformamide (10 ml) and n-heptyl bromide (4.1 g) were treated in a similar manner to that of Example 25-(1) to give oily ethyl 2-cyano-2-[2-methoxy-3-(o-tolyloxy)phenyl]-n-nonanate (6.8 g).

IR (Film): 2920, 1740, 1470, 1270, 1230 cm$^{-1}$

NMR (CCl$_4$): $\delta$0.67–2.40 (18H, m), 2.28 (3H, s), 3.90 (3H, s), 4.23 (2H, q, J=7 Hz), 6.57–7.27 (7H, m).

(2) A mixture of ethyl 2-cyano-2-[2-methoxy-3-(o-tolyloxy)phenyl]-n-nonanoate (6.7 g), hydriodic acid (58%, 10 ml) and acetic acid (30 ml) was refluxed under heating for 45 hours. The reaction mixture was concentrated under reduced pressure, and the residue was poured into water and extracted with diethyl ether. The extract was washed with aqueous sodium hydrogen sulfite and water in turn, dried and evaporated under reduced pressure. To the residue were added potassium hydroxide (5 g) and methanol (30 ml), and the mixture was refluxed under heating for an hour. After evaporation, the residue was dissolved in water, and the aqueous solution was washed with diethyl ether, acidified with conc. hydrochloric acid and then extracted with diethyl ether. The extract was washed with water, dried and evaporated under reduced pressure. The residue was purified by column chromatography (silica gel 90 g, benzene-ethyl acetate 1:1) to give 2-[2-hydroxy-3-(o-tolyloxy)phenyl]-n-nonanoic acid (4.3 g).

IR (Film): 3550, 2900, 1700, 1480, 1460, 1260, 1230, 1200 cm$^{-1}$.

NMR (DMSO-d$_6$): $\delta$0.75–2.69 (15H, m), 2.27 (3H, s), 3.97 (1H, t, J=7 Hz), 6.47–7.33 (7H, m), 9.83 (1H, br.s).

(3) Acetic anhydride (5 ml) was added to 2-[2-hydroxy-3-(o-tolyloxy)phenyl]-n-nonanoic acid (4.3 g), and the mixture was refluxed under heating for 10 minutes and evaporated under reduced pressure. The residue was purified by column chromatography (silica gel 60 g, benzene) to give 3-(n-heptyl)-7-(o-tolyloxy)-2,3-dihydrobenzofuran-2-one (3.0 g).

IR (Film): 1810, 1490, 1270, 1120 cm$^{-1}$.

NMR (CCl$_4$): $\delta$0.79–2.17 (15H, m), 2.27 (3H, s), 3.63 (1H, t, J=6 Hz), 6.60–7.27 (7H, m).

Analysis for C$_{22}$H$_{26}$O$_3$: Calculated: C: 78.07, H: 7.74; Found: C: 78.09, H: 7.70.

EXAMPLE 29

(1) A mixture of 2-(o-tolylthio)phenol (32.7 g), allyl bromide (27.5 g) and dried potassium carbonate (42 g) in methyl isobutyl ketone (400 ml) was refluxed under heating for 4 hours. The reaction mixture was treated in the same manner as Example 21-(1) to give oily 2-(o-tolylthio)-6-allylphenol (24.3 g), bp. 150°–162° C./0.7–0.8 mmHg.

IR (Film): 3420, 1440, 1240 cm$^{-1}$.

NMR (CCl$_4$): $\delta$2.43 (3H, s), 3.44 (2H, d, J=7 Hz), 4.87–5.23 (2H, m), 5.67–7.38 (8H, m).

(2) A mixture of 2-(o-tolylthio)-6-allylphenol (24 g) and potassium hydroxide (32 g) in methanol (100 ml) was stirred at 110° C. Methanol was distilled off from the mixture under ordinal pressure, and the mixture was stirred at 100° C. for an hour. The reaction mixture was cooled, acidified with conc. hydrochloric acid and extracted with diethyl ether. The extract was washed with water, dried and evaporated under reduced pressure to give oily 2-(o-tolylthio)-6-(1-propenyl)phenol (24.3 g).

IR (Film): 3400, 1440, 1240 cm$^{-1}$.

NMR (CDCl$_3$): $\delta$1.90 (3H, d, J=6 Hz), 2.43 (1H, s), 5.63–7.55 (9H, m).

(3) Ozone gas was introduced into a solution of 2-(o-tolylthio)-6-(1-propenyl)phenol (24.3 g) in a mixture of ethyl acetate (200 ml) and acetic acid (5 ml) at 3° C. for 1.5 hours. The excess of ozone was removed by air-bubbling and further decomposed with aqueous sodium hydrogen sulfite. The resultant organic layer was separated, washed with aqueous sodium hydrogen sulfite and water in turn, dried and then evaporated under reduced pressure. The oily residue was crystallized with ethanol to give yellow needles of 2-hydroxy-3-(o-tolylthio)benzaldehyde (12.2 g), mp. 42°–43° C.

IR (Nujol): 1660, 1640, 1470, 1440 cm$^{-1}$.

NMR (CDCl$_3$): $\delta$2.39 (3H, s), 6.73–7.48 (7H, m), 9.87 (1H, s), 12.50 (1H, s).

Analysis for C$_{14}$H$_{12}$O$_2$S: Calculated: C: 68.82, H: 4.95, S: 13.13; Found: C: 68.61, H: 4.89, S: 13.44.

(4) Sodium borohydride (850 mg) was added slowly to a suspension of 2-hydroxy-3-(o-tolylthio)benzaldehyde (11 g) in methanol (50 ml) at temperature below 15° C., and the mixture was stirred at the same temperature for 15 minutes and then at room temperature for 30 minutes. Methanol was distilled off from the reaction mixture under reduced pressure, and the residue was dissolved in water, acidified with conc. hydrochloric acid and extracted with ethyl acetate. The extract was washed with water, dried and evaporated under reduced pressure. The residue was crystallized with aqueous ethanol to give 2-hydroxy-3-(o-tolylthio)benzyl alcohol (8.45 g), mp. 75°–77° C.

IR (Nujol): 3400, 3330, 3230, 1470, 1450 cm$^{-1}$.

NMR (DMSO-d$_6$): $\delta$2.37 (3H, s), 3.37 (1H, br.s), 4.63 (3H, s), 6.70–7.40 (7H, m).

(5) A solution of potassium hydroxide (5.8 g) in water (30 ml) was added dropwise to a mixture of 2-hydroxy-3-(o-tolylthio)benzyl alcohol (8.3 g) and dimethyl sulfate (8.5 g) in 10 minutes at temperature below 60° C. with stirring, and the mixture was stirred at the same temperature for 10 minutes. The reaction mixture was treated in a similar manner to that of Example 21-(4). The resultant oily residue was purified by column chromatography (silica gel 150 g, benzene) to give oily 2-methoxy-3-(o-tolylthio)benzyl alcohol (8.5 g).

IR (Film): 3350, 1450, 1420, 1220, 1000 cm$^{-1}$.

NMR (CCl$_4$): $\delta$2.33 (3H, s), 3.39 (1H, br. s), 3.79 (3H, s), 4.56 (2H, s), 6.55–7.27 (7H, m).

(6) A mixture of 2-methoxy-3-(o-tolylthio)benzyl alcohol (8.5 g), thionyl chloride (4.8 ml) and pyridine (3 drops) in benzene (80 ml) was stirred at room temperature and then at 80° C. for 10 minutes. The reaction mixture was treated in a similar manner to that of Example 21-(6) to give oily o-tolyl 2-methoxy-3-chloromethylphenyl thioether (8.3 g).

IR (Film): 1460, 1420, 1000 cm$^{-1}$

NMR (CCl$_4$): $\delta$2.37 (3H, s), 3.95 (3H, s), 4.57 (2H, s), 6.55–7.40 (7H, m).

(7) Powdered sodium cyanide (1.5 g) was added all at once to a solution of o-tolyl 2-methoxy-3-chloromethylphenyl thioether (8.3 g) in dimethyl sulfoxide (40 ml), and the mixture was stirred for 15 minutes, poured into saturated aqueous solution of sodium chloride and extracted with diethyl ether. The extract was washed with water, dried and then evaporated under reduced pressure to give oily 2-[2-methoxy-3-(o-tolylthio)phenyl]acetonitrile (7.7 g).

IR (Film): 2250, 1460, 1420, 1000 cm$^{-1}$

NMR (CCl$_4$): δ2.33 (3H, s), 3.64 (2H, s), 3.90 (3H, s), 6.55–7.30 (7H, m).

(8) Sodium metal (0.7 g), dried ethanol (20 ml), 2-[2-methoxy-3-(o-tolylthio)phenyl]acetonitrile (7.7 g), ethyl carbonate (13 g) and toluene (50 ml) were treated in a similar manner to that of Example 22-(1) to give oily ethyl 2-cyano-2-[2-methoxy-3-(o-tolylthio)phenyl]acetate (9.4 g).

IR (Film): 2250, 1740, 1460, 1420, 1260, 1220 cm$^{-1}$.

NMR (CCl$_4$): δ1.24 (3H, t, J=7 Hz), 2.33 (3H, s), 3.91 (3H, s), 4.17 (2H, q, J=7 Hz), 4.94 (1H, s), 6.64–7.27 (7H, m).

(9) Sodium hydride (65%, 1.05 g), ethyl 2-cyano-2-[2-methoxy-3-(o-tolylthio)phenyl]acetate (9.4 g), methyl iodide (7.85 g) and dimethylformamide (40 ml) were treated in a similar manner to that of Example 22-(2) to give oily ethyl 2-cyano-2-[2-methoxy-3-(o-tolylthio)phenyl]propionate (10.0 g).

IR (Film): 2250, 1740, 1460, 1240 cm$^{-1}$.

NMR (CCl$_4$): δ1.25 (3H, t, J=7 Hz), 1.89 (3H, s), 2.33 (3H, s), 4.00 (3H, s), 4.23 (2H, q, J=7 Hz), 6.90–7.37 (7H, m).

(10) A mixture of ethyl 2-cyano-2-[2-methoxy-3-(o-tolylthio)phenyl]propionate (10 g) and hydriodic acid (58%, 12 ml) in acetic acid (24 ml) was refluxed under heating for 24 hours. After concentration, the residue was dissolved in aqueous sodium hydrogen sulfite and extracted with diethyl ether. The extract was washed with aqueous sodium hydrogen sulfite and water in turn, dried and evaporated under reduced pressure. To the residue was added acetic anhydride (10 ml), and the mixture was refluxed under heating for 10 minutes and evaporated under reduced pressure. The residue was subjected to column chromatography on silica gel (100 g) and eluted with benzene to give oily crude 3-methyl-7-(o-tolylthio)-2,3-dihydrobenzofuran-2-one (5.4 g). To this product (5.4 g) were added potassium hydroxide (1.5 g) and methanol (50 ml), and the mixture was refluxed under heating for an hour and concentrated under reduced pressure. The residue was crystallized with a mixture of benzene and n-hexane to give 2-[2-hydroxy-3-(o-tolylthio)phenyl]propionic acid (3.85 g), mp. 123°–125° C.

IR (Nujol): 3410, 1700, 1460, 1440 cm$^{-1}$.

NMR (DMSO-d$_6$): δ1.23 (3H, d, J=7 Hz), 2.23 (3H, s), 3.90 (1H, q, J=7 Hz), 6.60–7.25 (7H, m).

(11) A mixture of 2-[2-hydroxy-3-(o-tolylthio)phenyl]propionic acid (2.0 g) and acetic anhydride (5 ml) was refluxed under heating and evaporated under reduced pressure. The residue was purified by column chromatography (silica gel 30 g, benzene) to give 3-methyl-7-(o-tolylthio)-2,3-dihydrobenzofuran-2-one (1.4 g).

IR (Nujol): 1805, 1415, 1100, 1040 cm$^{-1}$.

NMR (CCl$_4$): δ1.50 (3H, d, J=8 Hz), 2.37 (3H, s), 3.62 (1H, q, J=8 Hz), 6.67–7.43 (7H, m).

EXAMPLE 30

A solution of m-chloroperbenzoic acid (1.3 g) in chloroform (20 ml) was added dropwise to a solution of 3-methyl-7-(2-chlorophenylthio)-2,3-dihydrobenzofuran-2-one (1.8 g) in chloroform (20 ml) in 10 minutes at a temperature below 6° C. with stirring, and the mixture was stirred at the same temperature for 30 minutes and then filtered. The organic layer was separated, washed with saturated aqueous sodium bicarbonate and water in turn, dried and evaporated under reduced pressure. The oily residue was crystallized with ethanol to give 3-methyl-7-(2-chlorobenzenesulfinyl)-2,3-dihydrobenzofuran-2-one (1.2 g), mp. 120°–122° C.

IR (Nujol): 1820, 1450, 1440 cm$^{-1}$

NMR (CDCl$_3$): δ1.55 (3H, d, J=8 Hz), 3.74 (1H, d, J=8 Hz), 7.07–8.20 (7H, m).

Analysis for C$_{15}$H$_{11}$O$_3$SCl: Calculated: C: 58.73, H: 3.61, S: 10.45, Cl: 11.56; Found: C: 58.73, H: 3.53, S: 10.39, Cl: 11.61.

EXAMPLE 31

(1) Pyridine (1 ml) was added to a solution of 2-(2-fluorophenylthio)phenol (9.4 g) in acetic anhydride (10 ml), and the mixture was stirred at room temperature for 30 minutes. The excess of acetic anhydride was distilled off under reduced pressure, and the resultant oily residue was dissolved in diethyl ether. The ether solution was washed with 10% hydrochloric acid and water in turn, dried and evaporated under reduced pressure to give oily 2-fluorophenyl 2-acetoxyphenyl thioether (11.2 g).

IR (Film): 1770, 1470, 1200 cm$^{-1}$.

NMR (CCl$_4$): δ2.17 (3H, s), 7.00–7.33 (8H, m).

(2) Powdered aluminum chloride (7.25 g) was added to 2-fluorophenyl 2-acetoxyphenyl thioether (11 g), and the mixture was allowed to exothermic reaction with stirring for 10 minutes. The reaction mixture was added to conc. hydrochloric acid and extracted with diethyl ether. The extract was washed with water, dried and evaporated under reduced pressure. The oily residue was purified by column chromatography (silica gel 120 g, benzene-n-hexane 3:2) to give oily 2-(2-fluorophenylthio)-6-acetylphenol (2.2 g).

IR (Film): 1640, 1430, 1320, 1250 cm$^{-1}$.

NMR (CCl$_4$): δ2.55 (3H, s), 6.53–7.64 (7H, m).

(3) Sodium borohydride (320 mg) was added to a solution of 2-(2-fluorophenylthio)-6-acetylphenol (2.2 g) in methanol (50 ml) in 5 minutes at 10° C., and stirred at 10° C. for 10 minutes and at room temperature for 10 minutes. The reaction mixture was evaporated under reduced pressure. To the residue was added 10% hydrochloric acid, and the mixture was extracted with diethyl ether. The extract was washed with water, dried and then evaporated under reduced pressure to give oily 1-[2-hydroxy-3-(2-fluorophenylthio)phenyl]ethanol (2.1 g).

IR (Film): 3380, 1470, 1450 cm$^{-1}$.

NMR (CDCl$_3$): δ1.84 (3H, d, J=7 Hz), 2.66 (1H, br. s), 5.11 (1H, q, J=7 Hz), 6.74–7.44 (8H, m).

(4) A solution of potassium hydroxide (1.6 g) in water (20 ml) was added slowly to a mixture of 1-[2-hydroxy-3-(2-fluorophenylthio)phenyl]ethanol (2.1 g) and dimethyl sulfate (2 g), and the mixture was stirred at room temperature for 30 minutes and at 60° C. for an hour. To the reaction mixture was added water, and the mixture was extracted with diethyl ether. The extract was washed with dil. aqueous solution of sodium hydroxide and water in turn, dried and evaporated under reduced pressure. The oily residue (1.8 g) was purified by column chromatography (silica gel 30 g, toluene) to give 1-[2-methoxy-3-(2-fluorophenylthio) phenyl]ethanol (1 g).

IR (Film): 3360, 1470, 1450, 1230, 1070, 1000 cm$^{-1}$.

NMR (CCl$_4$): δ1.39 (3H, d, J=6 Hz), 2.60 (1H, br. s), 3.83 (3H, s), 5.05 (1H, q, J=6 Hz), 6.83–7.33 (7H, m).

(5) A mixture of 1-[2-methoxy-3-(2-fluorophenylthio)phenyl]ethanol (1 g), thionyl chloride (500 mg) and pyridine (2 drops) in benzene (30 ml) was refluxed under heating for 30 minutes. The reaction mixture was evaporated under reduced pressure. To the residue was added water, and the mixture was extracted with diethyl ether. The extract was washed with dil. hydrochloric acid, saturated aqueous sodium bicarbonate and water in turn, dried and then evaporated under reduced pressure to give oily 2-fluorophenyl 2-methoxy-3-(1-chloroethyl)phenyl thioether (850 mg).

IR (Film): 1470, 1450, 1420, 1260, 1230 cm$^{-1}$

NMR (CCl$_4$): δ1.81 (3H, d, J=7 Hz), 4.00 (3H, s), 5.54 (1H, q, J=7 Hz), 6.94–7.50 (7H, m).

(6) Powdered sodium cyanide (132 mg) was added to a solution of 2-fluorophenyl 2-methoxy-3-(1-chloroethyl)phenyl thioether (800 mg) in dimethyl sulfoxide (10 ml) at room temperature, and stirred at 60° C. for 2 hours. The reaction mixture was poured into water and extracted with diethyl ether. The extract was washed with water, dried and evaporated under reduced pressure. The oily residue was purified by column chromatography (silica gel 15 g, toluene) to give oily 2-[2-methoxy-3-(2-fluorophehylthio)phenyl]propionitrile (400 mg).

IR (Film): 2260, 1480, 1430, 1240 cm$^{-1}$

NMR (CCl$_4$): δ1.59 (3H, d, J=8 Hz), 3.97 (3H, s), 4.14 (1H, q, J=8 Hz), 6.84–7.33 (7H, m).

(7) A solution of 2-[2-methoxy-3-(2-fluorophenylthio)phenyl]propionitrile (3.2 g) in hydriodic acid (58%, 20 ml) and acetic acid (40 ml) was refluxed under heating for 20 hours, and acetic acid was distilled off under reduced pressure. To the residue were added water and aqueous sodium bicarbonate, and the mixture was extracted with diethyl ether. The extract was washed with dil. aqueous sodium hydrogen sulfite and water in turn, dried and evaporated under reduced pressure. The oily residue (2 g) was purified by column chromatography (silica gel 40 g, toluene) to give oily 3-methyl-7-(2-fluorophenylthio)-2,3-dihydrobenzofuran-2-one (1.3 g).

IR (Film): 1800, 1480, 1460, 1030 cm$^{-1}$

NMR (CCl$_4$): δ1.57 (3H, d, J=8 Hz), 3.64 (1H, q, J=8 Hz), 6.90–7.50 (7H, m).

(8) 3-Methyl-7-(2-fluorophenylthio)-2,3-dihydrobenzofuran-2-one was hydrolyzed by treating with potassium hydroxide-methanol to give 2-[2-hydroxy-3-(2-fluorophenylthio)phenyl]propionic acid, mp. 116°–117° C.

IR (Nujol): 3400, 1690, 1470, 1450 cm$^{-1}$

NMR (DMSO-d$_6$): δ1.20 (3H, d, J=7 Hz), 4.03 (1H, q, J=7 Hz), 6.70–7.30 (7H, m)

Analysis for C$_{15}$H$_{13}$O$_3$SF: Calculated: C: 61.63, H: 4.48, S: 10.97, F: 6.50; Found: C: 61.53, H: 4.40, S: 11.10, F: 6.53.

EXAMPLE 32

(1) A solution of ethyl 2-cyano-2-[2-methoxy-3-(o-tolylthio)phenyl]acetate (4 g) in dimethylformamide (5 ml) was added dropwise to a solution of sodium hydride (purity 65%, 450 mg) in dimethylformamide (20 ml) in 10 minutes at temperature below 10° C. with stirring. After stirring the mixture at the same temperature for 10 minutes, n-hexyl bromide (3.85 g) was added to the mixture and stirred at 50° C. for an hour. After evaporation, water was added to the residue, and the mixture was extracted with diethyl ether. The extract was washed with water, dried and evaporated under reduced pressure to give oily ethyl 2-cyano-2-[2-methoxy-3-(o-tolylthio)phenyl]octanoate (5 g).

IR (Film): 2250, 1740, 1460, 1420, 1230 cm$^{-1}$.

NMR (CCl$_4$): δ0.74–2.31 (13H, m), 1.15 (3H, t, J=8 Hz), 2.33 (3H, s), 3.97 (3H, s), 4.23 (2H, q, J=8 Hz), 6.74–7.37 (7H, m)

(2) A solution of ethyl 2-cyano-2-[2-methoxy-3-(o-tolylthio)phenyl]octanoate (5 g) in hydriodic acid (58%, 20 ml) and acetic acid (40 ml) was refluxed under heating for 24 hours. The reaction mixture was treated in a similar manner to that of Example 31-(7) to give oily 3-n-hexyl-7-(o-tolylthio)-2,3-dihydrobenzofuran-2-one (1.7 g).

IR (Film): 2930, 1810, 1440, 1050 cm$^{-1}$

NMR (CCl$_4$): δ0.70–2.20 (13H, m), 2.42 (3H, s), 3.63 (1H, t, J=6 Hz), 6.77–7.40 (7H, m).

Analysis for C$_{21}$H$_{24}$O$_2$S: Calculated: C: 74.08, H: 7.10, S: 9.42; Found: C: 74.15, H: 7.09, S: 9.00.

(3) 3-n-Hexyl-7-(o-tolylthio)-2,3-dihydrobenzofuran-2-one was hydrolyzed by treating with potassium hydroxide-methanol to give 2-[2-hydroxy-3-(o-tolylthio)phenyl]octanoic acid, mp. 90°–91° C.

IR (Nujol): 3420, 1700, 1470, 1450 cm$^{-1}$

NMR (DMSO-d$_6$): δ0.67–2.17 (13H, m), 2.35 (3H, s), 3.97 (1H, t, J=7 Hz), 6.70–7.33 (7H, m).

Analysis for C$_{21}$H$_{26}$O$_3$S: Calculated: C: 70.36, H: 7.31, S: 8.95; Found: C: 70.39, H: 7.35, S: 8.82.

EXAMPLE 33

(1) A solution of 2-[2-methoxy-3-(o-tolylthio)phenyl]acetonitrile (5.9 g) in hydriodic acid (58%, 15 ml) and acetic acid (30 ml) was refluxed under heating for 17 hours. After concentration, water and aqueous sodium hydrogen sulfite were added to the residue and extracted with diethyl ether. The extract was washed with dil. aqueous sodium hydrogen sulfite and water in turn and evaporated. To the residue was added a solution of potassium hydroxide (2 g) in methanol (50 ml), and the mixture was refluxed under heating for 2 hours. Methanol was distilled off under reduced pressure, and the residue was dissolved in water, washed with diethyl ether, acidified with conc. hydrochloric acid and then extracted with diethyl ether. The extract was washed with water, dried and exaporated under reduced pressure to give crude 2-[2-hydroxy-3-(o-tolylthio)phenyl]acetic acid (4.2 g). To this product was added acetic anhydride (5 ml), and the mixture was refluxed under heating. The reaction mixture was evaporated, and the resultant oily residue was crystallized with ethanol to give pale yellow needles of 7-(o-tolylthio)-2,3-dihydrobenzofuran-2-one (1.58 g), mp. 108°–109° C.

IR (Nujol): 1800, 1460, 1440, 1080 cm$^{-1}$.

NMR (DMSO-d$_6$): δ2.37 (3H, s), 4.00 (2H, s), 6.90–7.40 (7H, m).

Analysis for C$_{15}$H$_{12}$O$_2$S: Calculated: C: 70.29, H: 4.72, S: 12.51; Found: C: 70.16, H: 4.54, S: 12.78.

(2) Thus obtained 7-(o-tolylthio)-2,3-dihydrobenzofuran-2-one was hydrolyzed by treating with potassium hydroxide-methanol to give 2-[2-hydroxy-3-(o-tolylthio)phenyl]acetic acid, mp. 96°–97° C.

IR (Nujol): 3400, 1710, 1690, 1460, 1450 cm$^{-1}$.

NMR (DMSO-d$_6$): δ2.36 (3H, s), 3.64 (2H, s), 6.67–7.40 (7H, m).

Analysis for C$_{15}$H$_{14}$O$_3$S: Calculated: C: 65.67, H: 5.14, S: 11.69; Found: C: 65.12, H: 5.12, S: 11.76.

We claim:

1. A compound of the formula:

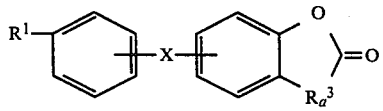

wherein
R[1] is hydrogen, halogen, hydroxy, lower alkyl or lower alkoxy,
$R_a{}^3$ is $C_{1-8}$ alkylene or $C_{1-8}$ alkylene substituted with lower alkyl, cyano, amino or protected amino group where the protective group is ar(lower)alkyl, lower alkanoyl, lower alkoxycarbonyl, ar(lower)alkoxycarbonyl, succinoyl or phthaloyl,
X is O, S, SO or $SO_2$, or a pharmaceutically acceptable salt thereof.

2. A compound according to claim 1, wherein
R[1] is halogen or lower alkyl,
$R_a{}^3$ is $C_{1-8}$ alkylene or $C_{1-8}$ alkylene substituted with lower alkyl, and
X is O or S.

3. The compound according to claim 2, which is
7-(o-tolyloxy)-2,3-dihydrobenzofuran-2-one,
7-(2-chlorophenoxy)-2,3-dihydrobenzofuran-2-one,
3-methyl-7-(2-chlorophenoxy)-2,3-dihydrobenzofuran-2-one,
3-methyl-7-(o-tolyloxy)-2,3-dihydrobenzofuran-2-one,
3-ethyl-7-(o-tolyloxy)-2,3-dihydrobenzofuran-2-one,
3-methyl-7-(2-fluorophenoxy)-2,3-dihydrobenzofuran-2-one,
7-(2-chlorophenylthio)-2,3-dihydrobenzofuran-2-one,
3-methyl-7-(2-chlorophenylthio)-2,3-dihydrobenzofuran-2-one, or
3-methyl-7-(o-tolylthio)-2,3-dihydrobenzofuran-2-one.

4. A pharmaceutical composition, comprising an effective amount of a compound of claim 1, as an effective ingredient which possesses antiinflammatory, analgesic and antipyretic properties, in association with a pharmaceutically acceptable, substantially notoxic carrier or excipinet.

5. A method for treating an inflammation, which comprises: administering an effective amount of the compound of claim 1 to human beings.

6. A method for treating a headache which comprises:
administering an effective amount of the compound of claim 1 to human beings.

7. A method for treating a toothache which comprises:
administering an effective amount of the compound of claim 1 to human beings.

8. A method for treating pyrexia which comprises:
administering an effective amount of the compound of claim 1 to human beings.

* * * * *